(12) United States Patent
Izumori et al.

US007906487B2

(10) Patent No.: US 7,906,487 B2
(45) Date of Patent: Mar. 15, 2011

(54) METHOD OF UTILIZING PHYSIOLOGICAL ACTIVITY OF RARE SACCHARIDE AND COMPOSITION CONTAINING RARE SACCHARIDE

(75) Inventors: Ken Izumori, Takamatsu (JP); Masaaki Tokuda, Takamatsu (JP); Toshifumi Itano, Takamatsu (JP); Osamu Miyamoto, Kagawa (JP); Toshihiko Ishida, Takamatsu (JP); Koji Murao, Takamatsu (JP); Taizo Tasaka, Takamatsu (JP); Gan Muneuchi, Kagawa (JP); Fuminori Yamaguchi, Kagawa (JP); Terukazu Tanaka, Takamatsu (JP); Masaaki Ueki, Kagawa (JP); Kazuyuki Hirooka, Kagawa (JP); Tomohiko Taminato, Takamatsu (JP); Mohammad Akram Hossain, Kagawa (JP); Keiji Tsusaki, Kurashiki (JP); Takeo Takahashi, Marugame (JP); Mitsuhiro Nagata, Takamatsu (JP); Yutaka Ishida, Takamatsu (JP)

(73) Assignees: Fushimi Pharmaceutical Co., Ltd., Marugame-shi (JP); Teikoku Seiyaku Co., Ltd., Higashikagawa-shi (JP); National University Corporation Kagawa University, Takamatsu-shi (JP); Kabushiki Kaisha Hayashibara Seibutsu Kagaku Kenkyujo, Okayama-shi (JP)

(*) Notice: Subject to any disclaimer, the term of this patent is extended or adjusted under 35 U.S.C. 154(b) by 413 days.

(21) Appl. No.: 10/515,018

(22) PCT Filed: May 22, 2003

(86) PCT No.: PCT/JP03/06405
§ 371 (c)(1),
(2), (4) Date: Jun. 21, 2005

(87) PCT Pub. No.: WO03/097820
PCT Pub. Date: Nov. 27, 2003

(65) Prior Publication Data
US 2005/0245459 A1 Nov. 3, 2005

(30) Foreign Application Priority Data
May 22, 2002 (JP) ................... 2002-148370

(51) Int. Cl.
*A61K 31/70004* (2006.01)
*A61K 31/70* (2006.01)
(52) U.S. Cl. ........................ 514/23; 536/124
(58) Field of Classification Search ............ 514/23; 536/124
See application file for complete search history.

(56) References Cited

U.S. PATENT DOCUMENTS
2005/0074819 A1 4/2005 Inoue et al.

OTHER PUBLICATIONS

Pratt et al. (Journal of Cellular Physiology, (1994) vol. 161, No. 3, pp. 580-588).*
Abstract of Shiseido Co Ltd (JP 2000103728; Apr. 11, 2000).*
Izumori cet al., (Foods and Development (Shokuhin to Kaihatsu), Processing, vol. 38, No. 1, pp. 66-69, Jan. 1, 2003).*
Gura (Science, 1997, 278(5340): 1041-1042).*
Jain (Sci. Am., 1994, 271:58-65).*
Curti (Crit. Rev. in oncology/Hematology, 1993, 14:29-39).*
Matsuo et al. (Asia Pacific J Clin Nutr (2001) 10(3): 233-237).*
Thompson et al.(Arterioscler Thromb Vasc Biol 1991;11;327-333).*
Gaal et al (Diabetes Care. Feb. 1988;11(2):103-6).*
K. Sekiya, *Anti-oxidation Function of Rare Sugars such as D-psicose*, Nihon Shokuhin Kagaku Kogakukai Taikai Koenshu, vol. 48, p. 107, 2001.
S.E. Pratt et al., *Evidence That Modulation of Glucose Transporter Intrinsic Activity Is the Mechanism Involved in the Allose-Mediated Depression of Hexose Transport in Mammalian Cells*, Journal of Cellular Physiology, vol. 161, No. 3, pp. 580-588, 1994.
T. Matsuo et al., *D-Psicose Is a Rare Sugar That Provides No Energy to Growing Rats*, Journal Nutr. Sci. Vitaminol, vol. 48, No. 1, pp. 77-80, 2002, Tokyo.
K. Izumori et al., *Foods and Development (Shokuhin to Kaihatsu)*, Processing, vol. 38, No. 1, pp. 66-69, Jan. 1, 2003.
M. Tokuda et al., *Organ Protection against Ischemea Based on D-allose Action of Suppressing Production of Active Oxygen*, Seikagaku, vol. 74, No. 8, p. 1063, 4P-599, Aug. 25, 2002.
Keizo Sekitani, Nihon Shokuhin Kagaku Kogakukai Taikai Koenshu, vol. 48, p. 107, 2001. Cited in the international search report.
S. E. Pratt et al.; J. Cell. Physiol., vol. 161, No. 3, pp. 580-588, 1994. Cited in the international search report.
T. Matuo et al.; J. Nutr. Sci. Vitaminol (Tokyo); vol. 48, No. 1, pp. 77-80. Feb. 2002. Cited in the international search report.
Ken Nanimori et al.; Food Processing, vol. 38, No. 1, pp. 66-39. Jan. 1, 2003. Cited in the international search report. Masaaki Tokuda et al.; Seikagaku, vol. 74, No. 8, p. 1063, 4P-599, Aug. 25, 2002. Cited in the international search report.
Wesselmann, Ursula; "Chronic Nonmalignant Nociceptive Pain Syndromes"; Surgical Management of Pain, Thieme Medical Publishers. Inc, 2002; p. 365

* cited by examiner

*Primary Examiner* — Shaojia Anna Jiang
*Assistant Examiner* — Michael C Henry
(74) *Attorney, Agent, or Firm* — Westerman, Hattori, Daniels & Adrian, LLP

(57) ABSTRACT

A method of utilizing the physiological activity of a rare saccharide, wherein physiological-activity sensitive cells are treated with the rare saccharide to modify the function of the cells. A composition containing, as an active ingredient, a rare saccharide which is introduced into physiological-activity sensitive cells and has an effect of modifying the function of the cells. The cells are human cells. The composition is a functional food, a drug, or a cosmetic. The rare saccharide is a rare saccharide belonging to aldose and/or ketose. The aldose is D-allose, and the cells are selected from the group consisting of cancer-cell proliferation inhibitory activity sensitive cells and active-oxygen production inhibitory activity sensitive cells. The ketose is D-psicose, and the cells are selected from the group consisting of chemokine secretion inhibitory activity sensitive cells, microglia migration inhibitory activity sensitive cells, and hypoglycemic activity sensitive cells.

3 Claims, 28 Drawing Sheets

Fig.18

|  | Allose 150mg (0.5mg/g) | Allose 60mg (0.2mg/g) | Allose 30mg (0.1mg/g) | Allose 15mg (0.05mg/g) | Glucose 60mg (0.2mg/g) | physiological saline |
|---|---|---|---|---|---|---|
| 1 | 100 | 84 | 78 | 0 | 92 | 7 |
| 2 | 93 | 100 | 71 | 81 | 83 | 74 |
| 3 | 91 | 40 | 100 | 25 | 100 | 68 |
| 4 | 56 | 100 | 47 | 97 | 100 | 70 |
| 5 | 72 | 93 | 66 | 100 | 0 | 0 |
| 6 | 100 | 82 | 100 | 48 | 14 | 0 |
| 7 | 37 | 100 | 61 | 100 | 72 | 86 |
| 8 | 100 | 100 | 91 | 94 | 0 | 93 |
| 9 | 25 | 91 | 100 | 99 | 100 | 48 |
| 10 | 94 | 13 | 41 | 30 | 10 | 69 |
| 11 | 79 | 100 | 46 | 68 | 0 | 87 |
| 12 | 98 | 17 | 48 | 47 | 34 | 81 |
| 13 | 59 | 88 | 99 | 57 | 92 | 75 |
| 14 | 73 | 100 | 93 | 62 | 41 | 0 |
| 15 | 91 | 81 | 97 | 29 | 68 | 0 |
| Average | 77.9 | 79.2 | 75.9 | 62.5 | 53.7 | 50.5 |

Fig.19

|  | Number | Average | Unbiased estimate of population variance | Standard deviation | Standard error |
|---|---|---|---|---|---|
| 150mg(0.5mg/g) | 15 | 77.86666667 | 576.2666667 | 24.00555491 | 6.198207626 |
| 60mg(0.2mg/g) | 15 | 79.26666667 | 916.0666667 | 30.26659325 | 7.814800772 |
| 30mg(0.1mg/g) | 15 | 75.86666667 | 522.552381 | 22.85940465 | 5.902272901 |
| 15mg(0.05mg/g) | 15 | 62.46666667 | 1047.980952 | 32.37253392 | 8.358552316 |
| Glucose | 15 | 53.73333333 | 1674.92381 | 40.92583303 | 10.56700465 |
| physiological saline | 15 | 50.53333333 | 1400.695238 | 37.42586322 | 9.663316332 |
| Total | 90 | 66.62222222 | 1102.799501 | 33.20842515 | 3.500475366 |

Fisher's PLSD risk-reward ratio 5%

| | difference in average | cut off value | p value | | |
|---|---|---|---|---|---|
| 150mg(0.5mg/g),60mg(0.2mg/g) | -1.4 | 23.22597868 | 0.904873856 | | |
| 150mg(0.5mg/g),30mg(0.1mg/g) | 2 | 23.22597868 | 0.864446763 | | |
| 150mg(0.5mg/g),15mg(0.05mg/g) | 15.4 | 23.22597868 | 0.190903671 | | |
| 150mg(0.5mg/g),Glucose | 24.13333333 | 23.22597868 | 0.04188096 | S | ⊛ |
| 150mg(0.5mg/g),saline | 27.33333333 | 23.22597868 | 0.021640642 | S | ⊛ |
| 60mg(0.2mg/g),30mg(0.1mg/g) | 3.4 | 23.22597868 | 0.771686111 | | |
| 60mg(0.2mg/g),15mg(0.05mg/g) | 16.8 | 23.22597868 | 0.154031175 | | |
| 60mg(0.2mg/g),Glucose | 25.53333333 | 23.22597868 | 0.031585637 | S | ⊛ |
| 60mg(0.2mg/g),saline | 28.73333333 | 23.22597868 | 0.015937505 | S | ⊛ |
| 30mg(0.1mg/g),15mg(0.05mg/g) | 13.4 | 23.22597868 | 0.254511205 | | |
| 30mg(0.1mg/g),Glucose | 22.13333333 | 23.22597868 | 0.061524683 | | |
| 30mg(0.1mg/g),saline | 25.33333333 | 23.22597868 | 0.032905893 | S | ⊛ |
| 15mg(0.05mg/g),Glucose | 8.733333333 | 23.22597868 | 0.456700023 | | |
| 15mg(0.05mg/g),saline | 11.93333333 | 23.22597868 | 0.309840918 | | |
| Glucose,saline | 3.2 | 23.22597868 | 0.784769336 | | |

Fig.41

| | | |
|---|---|---|
| Aldotetrose (4) | DEry | D-Erythrose |
| | DThr | D-Threose |
| | LEry | L-Erythrose |
| | LThr | L-Threose |
| Ketotetrose (2) | DEry | D-Erythrulose |
| | LEry | L-Erythrulose |
| Tetritol (3) | D,LEry | D-,L-Erythritol |
| | DThr | D-Threitol |
| | LThr | L-Threitol |
| (Tetroses 9) | | |
| Aldopentose (8) | DRib | D-Ribose |
| | DAra | D-Arabinose |
| | DXyl | D-Xylose |
| | DLyx | D-Lyxose |
| | LRib | L-Ribose |
| | LAra | L-Arabinose |
| | LXyl | L-Xylose |
| | LLyx | L-Lyxose |
| Ketopentose (4) | DRib | D-Ribulose |
| | DXyl | D-Xylulose |
| | LRib | L-Ribulose |
| | LXy | L-Xylulose |
| Pentitol (4) | D,LRib | D-Ribitol,L-Ribitol |
| | DAra | D-Arabitol |
| | D,LXyl | D-Xylitol,L-Xylitol |
| (Pentoses 16) | LAra | L-Arabitol |
| Aldohexose (16) | DAll | D-Allose |
| | DAlt | D-Altrose |
| | DGlu | D-Glucose |
| | DMan | D-Mannose |
| | DGul | D-Gulose |
| | DIdo | D-Idose |
| | DGal | D-Galactose |
| | DTal | D-Talose |
| | LAll | L-Allose |
| | LAlt | L-Altrose |
| | Lglu | L-Glucose |
| | DMan | L-Mannose |
| | LGul | L-Gulose |
| | LIdo | L-Idose |
| | LGal | L-Galactose |
| | LTal | L-Talose |
| Ketohexose (8) | DFru | D-Fructose |
| | DPsi | D-Psicose |
| | DSor | D-Sorbose |
| | DTag | D-Tagatose |
| | LFru | L-Fructose |
| | LPsi | L-Psicose |
| | LSor | L-Sorbose |
| | LTag | L-Tagatose |
| Hexitol (10) | D,LAll | D-Allitol,L-Allitol |
| | DAlt,DTal | D-Altritol,D-Talitol |
| | DGlu,LGul | D-Glucitol,L-Gulitol |
| | DMan | D-Mannitol |
| | DGul,LGlu | D-Gulitol,L-Glucitol |
| | DIdi | D-Iditol |
| | D,LGal | D-Galactitol,L-Galactitol |
| | LAlt,LTal | L-Altritol,L-Talitol |
| | LMan | L-Mannitol |
| (Hexoses 34) | LIdi | L-Iditol |

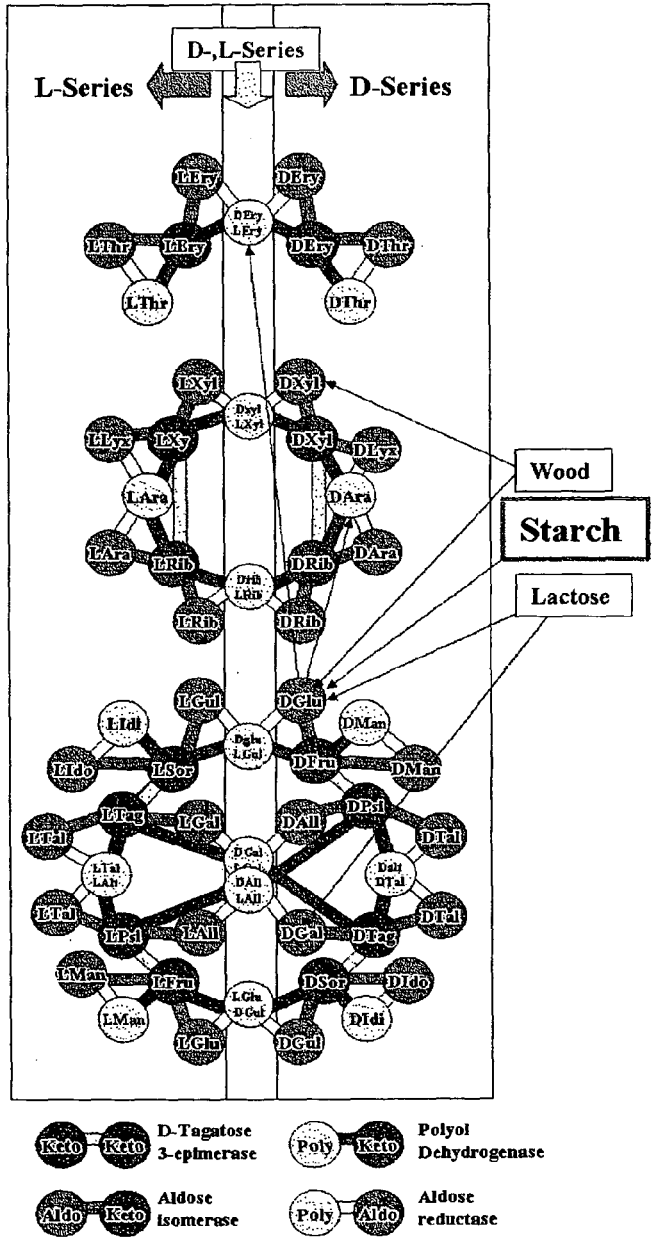

Biosynthesis strategy for all monosaccharides using Izumoring

METHOD OF UTILIZING PHYSIOLOGICAL ACTIVITY OF RARE SACCHARIDE AND COMPOSITION CONTAINING RARE SACCHARIDE

TECHNICAL FIELD

The present invention relates to a method of utilizing the physiological activity of a rare saccharide (rare sugar) and a composition containing a rare saccharide as an active ingredient, in particular, a functional food, a drug, or a cosmetic.

BACKGROUND ART

Monosaccharides are mainly grouped into aldose having a polyhydroxyl aldehyde structure, ketose having a polyhydroxyl ketone structure, and sugar alcohols obtained by reducing the aldose and the ketose. Also, monosaccharides are classified depending on amounts by which they are present in the natural world. More specifically, a rare saccharide is defined as "a saccharide that is rarely present in the natural world" by International Society of Rare Sugars, i.e., it is a monosaccharide present in the natural world in very small amount. Many of rare saccharides generally have small yields in synthesis reactions based on organic chemical synthesis methods. For that reason, properties of many rare saccharides are still unknown. In the current state, therefore, such rare saccharides as aldohexose (aldose of hexose), including D-allose, have many not-yet-known properties.

In addition to D-allose, examples of rare saccharides belonging to aldohexose include D-gulose, D-idose, D-talose, D-altrose, L-mannose, L-glucose, and L-galactose. The above-described situations are similarly applied to such rare saccharides as ketohexose (ketose of hexose), including D-psicose. Examples of rare saccharides belonging to ketohexose include D-psicose, L-psicose, D-sorbose, L-sorbose, D-tagatose, L-tagatose, and L-fructose.

In connection with the relationships between saccharides and cancers, there have hitherto been known polysaccharides that are effective in preventing cancers, as disclosed in Patent Reference 1, for example. Also, it has been reported that an oligosaccharide acts to keep the intestine in order and therefore it is effective in relieving constipation for protection against a colon cancer. Further, there have recently been publicized reports indicating a cancer inhibitory effect of polysaccharides, such as agaricus, and discussing the relations between saccharide chains and metastasis of cancers.

On the other hand, as an example utilizing the properties of saccharides against active oxygen, an active oxygen inhibitor containing a polysaccharide with active-oxygen inhibitory properties is known as disclosed in, e.g., Patent Reference 2.

Among rare saccharides, psicose is ketohexose (ketose of hexose). There are known two optical isomers, i.e., D-psicose and L-psicose. D-psicose is a known substance, but it is rarely present in the natural world. Therefore, D-psicose is a "rare saccharide" according to the definition by International Society of Rare Sugars. With recent commercialization of epimerase (see, e.g., Patent Reference 3), however, D-psicose has become relatively easily available although it is still expensive. Patent Reference 3 also suggests that prepared D-psicose can be effectively utilized as raw materials, intermediates, etc. for sweeteners, carbon sources for fermentation, reagents, cosmetic and medicines. Further, Patent Reference 3 discloses that the sweeteners can be utilized to add sweetness and to improve taste of oral ingesta, such as food and drink, feed, dentifrice, and internal medicines, but it does not include detailed disclosure regarding the use as an edible additive. With regards to L-psicose, i.e., an optical isomer of D-psicose, Patent Reference 4, for example, discloses in detail that L-psicose can be utilized as an edible additive.

| | |
|---|---|
| Patent Reference 1 | Japanese Patent Laid-Open No. 5-112455 |
| Patent Reference 2 | Japanese Patent Laid-Open No. 7-285871 |
| Patent Reference 3 | Japanese Patent Laid-Open No. 6-125776 |
| Patent Reference 4 | Japanese Patent Laid-Open No. 57-129671 |

DISCLOSURE OF THE INVENTION

In view of physiological activities of rare saccharides, the inventors have begun to examine and support those physiological activities based on experiments using cells. The 21st century is called a century of life science, and researches of DNA and protein are internationally progressed at present. Although, among saccharides handled in post-genome researches, main attention is focused on saccharide chains, the inventors have continued researches with attention paid to "rare saccharides" from the viewpoint of confirming whether the rare saccharides have physiological activities or not. As the background of the present invention, comprehensive researches regarding production of rare saccharides have been continuously conducted for long years, and mass-production technology of a part of rare saccharides have been established in recent years.

An object of the present invention is to provide a method of utilizing the physiological activity of a rare saccharide, in particular D-allose and D-psicose, and to produce a functional food, a drug, etc. utilizing the physiological activity of the rare saccharide.

The present invention resides in the method of utilizing the physiological activity of a rare saccharide, as stated in (1) to (9) given below.

(1) A method of utilizing the physiological activity of a rare saccharide, wherein physiological-activity sensitive cells are treated with the rare saccharide to modify the function of the cells.

(2) In the method of above (1), the cells are human cells.

(3) In the method of above (1) or (2), a composition containing a rare saccharide as an active ingredient is used as the rare saccharide.

(4) In the method of above (3), the composition is a functional food, a drug, or a cosmetic.

(5) In the method of any one of above (1) to (4), the rare saccharide is a rare saccharide belonging to aldose and/or ketose.

(6) In the method of above (5), the aldose is D-allose.

(7) In the method of above (6), the cells are selected from the group consisting of cancer-cell proliferation inhibitory activity sensitive cells and active-oxygen production inhibitory activity sensitive cells.

(8) In the method of above (5), the ketose is D-psicose.

(9) In the method of above (8), the cells are selected from the group consisting of chemokine secretion inhibitory activity sensitive cells, microglia migration inhibitory activity sensitive cells, and hypoglycemic activity sensitive cells.

Also, the present invention resides in a composition containing a rare saccharide as an active ingredient, as stated in (10) to (17) given below.

(10) A composition containing, as an active ingredient, a rare saccharide which has an effect of affecting physiological-activity sensitive cells to modify the function of the cells.

(11) In the composition of above (10), the cells are human cells.
(12) In the composition of above (10) or (11), the rare saccharide is a rare saccharide belonging to aldose and/or ketose.
(13) In the composition of above (12), the aldose is D-allose.
(14) In the composition of above (13), the cells are selected from the group consisting of cancer-cell proliferation inhibitory activity sensitive cells and active-oxygen production inhibitory activity sensitive cells.
(15) In the composition of above (12), the ketose is D-psicose.
(16) In the composition of above (15), the cells are selected from the group consisting of chemokine secretion inhibitory activity sensitive cells, microglia migration inhibitory activity sensitive cells, and hypoglycemic activity sensitive cells.
(17) In the composition of any one of above (10) to (16), the composition is a functional food, a drug, or a cosmetic.

BRIEF DESCRIPTION OF THE DRAWINGS

FIG. 18 is a table showing all data of survival areas (%), measured in Example 7, regarding a skin-flap ischemia-reperfusion injury relieving effect of D-allose.

FIG. 19 is a table showing results of variance analysis (one-dimensional arrangement), measured in Example 7, regarding the skin-flap ischemia-reperfusion injury relieving effect of D-allose.

FIG. 41 shows an Izumoring linkage map.

BEST MODE FOR CARRYING OUT THE INVENTION

The term "rare saccharide" can be defined as a rare saccharide that exists in the natural world just in trace amount. The rare saccharide employed in the present invention is one based on that definition, and is preferably D-allose belonging to aldose or D-psicose belonging to ketose. There are seven kinds of monosaccharides that exist in the natural world in large amount, i.e., D-glucose, D-fructose, D-galactose, D-mannose, D-ribose, D-xylose, and L-arabinose. Monosaccharides other than those ones are all rare saccharides. Also, sugar alcohols are obtained by reducing monosaccharides, and D-sorbitol exists in the natural world in relatively large amount. However, other sugar alcohols than D-sorbitol exist in small amount. For that reason, the other sugar alcohols than D-sorbitol are also defined as rare saccharides according to the present invention. Those rare saccharides have been difficult to obtain in the past, but they can now be produced with development of a method for producing the rare saccharides from the monosaccharides that exist in the natural world abundantly.

Relationships among the monosaccharides will be described in detail below with reference to Izumoring proposed for the purpose of easier understanding of the relationships.

FIG. 41 shows the entirety of Izumoring representing the linkage among all monosaccharides having carbon numbers of 4 to 6 on the basis of production processes and molecular structures (D-type and L-type). It is understood from FIG. 41 that the monosaccharides having carbon numbers of 4 to 6 are all linked with one another. In other words, as seen from the entire linkage map, the monosaccharides in the Izumoring of C6 are linked with one another, the monosaccharides in the Izumoring of C5 are linked with one another, and the monosaccharides in the Izumoring of C4 are linked with one another, while the Izumorings of C4, C5 and C6 are linked with one another. That concept is important. The number of carbons is reduced primarily by using zymotechnics. Another feature is that the monosaccharides having different carbon numbers are all linked with one another in the large linkage map. Additionally, it can be understood that there is no utility value.

Figure 42:
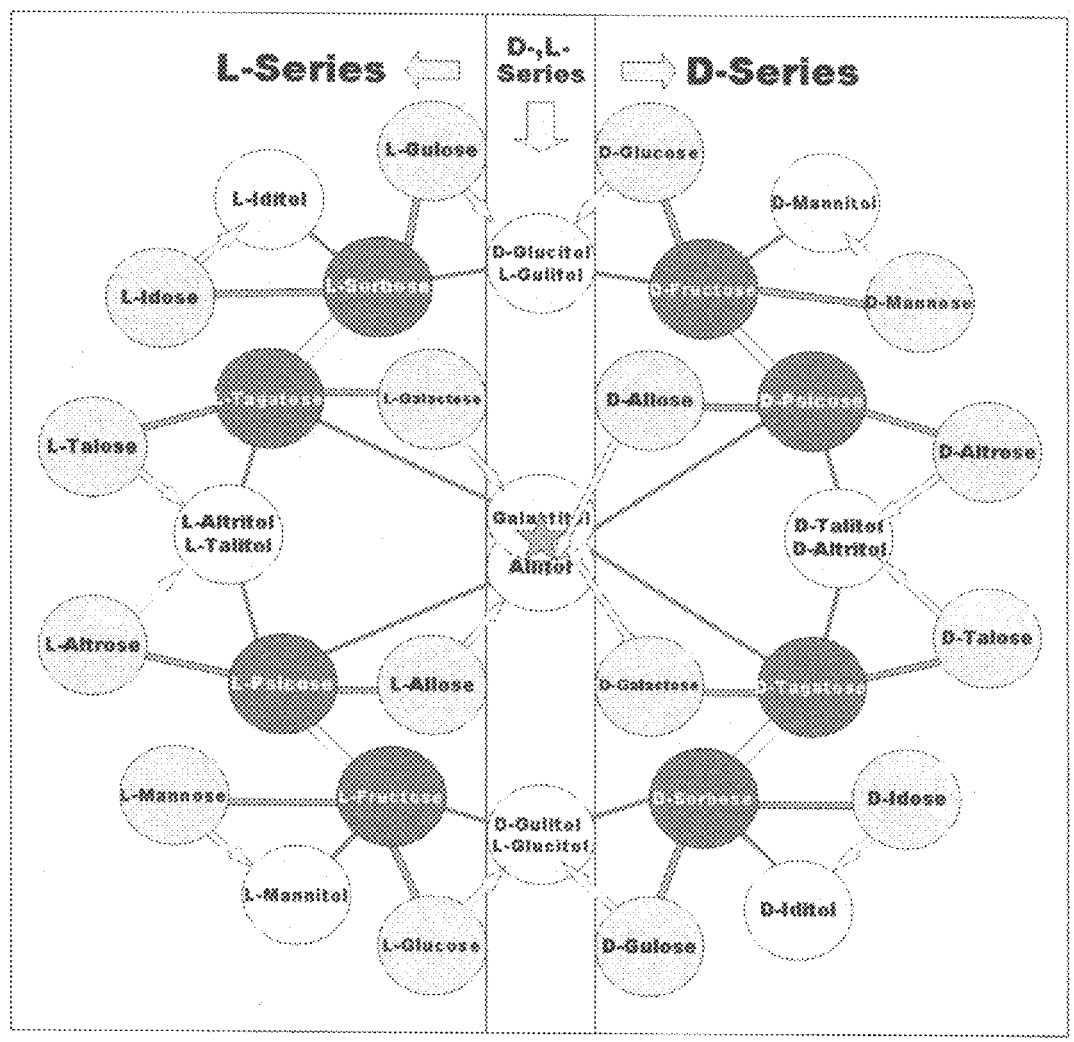
FIG. 42 shows Izumoring of C6, in a lower are of FIG. 41, for more detailed explanation.

As shown in a lower area of FIG. 41 and FIG. 42, the Izumoring of the monosaccharides having the carbon number of 6 (i.e., hexose) includes 34 kinds of monosaccharides having the carbon number of 6 (i.e., hexose) in total, namely 16 kinds of aldose, 8 kinds of ketose, and 10 kinds of sugar alcohols. From studies including ones conducted by the inventors, it is known that those monosaccharides are convertible from one to another through reactions of oxidizing/reducing enzymes, reactions of aldose isomerization enzymes, and aldose reducing enzymes. In the state of studies up to now, however, an upper group, a meddle group, and a lower group in FIG. 41 are not yet linked with one another through enzyme reactions. Stated another way, D-glucose (grape sugar) and D-fructose both belonging to the upper group are monosaccharides abundant in the natural world and are inexpensive, but it has been impossible to synthesize rare saccharides from those monosaccharides. During the progress of the studies, however, the inventors discovered an enzyme interconnecting those monosaccharides and the rare saccharides. That discovery had begun from the fact that utterly unexpected D-sorbose was discovered in a culture solution containing a germ that has an enzyme for producing D-tagatose from galactitol. As a result of studying the cause of such a phenomenon, the inventors have found that the above-mentioned germ produces an enzyme called D-tagatose 3-epimerase (DTE).

Further, as seen from the lower area of FIG. 41 and FIG. 42, DTE is an enzyme interconnecting D-tagatose and D-sorbose which have been disconnected from each other in the past. To be more surprisingly, it has been confirmed that DTE is an enzyme epimerizing a group at position 3 of all kinds of ketose, and it is a unique enzyme having such a very wide range of substrate peculiarity as acting interconnections between D-fructose and D-psicose, L-sorbose and L-tagatose, D-tagatose and D-sorbose, and L-psicose and L-fructose, which have faced a difficulty in synthetic interconnection up to now. Thus, the discovery of DTE has succeeded in linking all the monosaccharides with one another in the form of a ring, and has completed a structural expression of knowledge of the monosaccharides. That entire ring is named "Izumoring".

Looking FIG. 42 in more detail, it is understood that there are L-types on the left side, D-types on the right side, and DL-types at the center, and that the L-types and the D-types are point-symmetrical about the center (indicated by a star mark) of the ring. For example, D-glucose and L-glucose are point-symmetrical about the center. Further, a value of the Izumoring resides in that it serves also as a design drawing for production of all monosaccharides. In trying to produce L-glucose from D-glucose as a start point, for example, the Izumoring indicates that L-glucose can be produced from D-glucose through successive steps of isomerization→epimerization→reduction→ oxidation→ epimerization→isomerization.

In other words, FIG. 42 shows the relationships between the saccharides abundant in the natural world and the rare saccharides existing just in trace amount in the form of Izumoring covering the monosaccharides having the carbon number of 6 (i.e., hexose). D-glucose, D-fructose, D-mannose, and D-galactose, which can be produced from milk sugar (lactose) contained in milk, exist in the natural world in large amount, while the other monosaccharides are classified as rare saccharides that exist just in trace amount. With the discovery of DTE, it has become possible to produce D-fructose and D-psicose from D-glucose, and to further produce D-allose, allitol, and D-tallitol.

To summarize, the useful meanings of the Izumoring covering the monosaccharides having the carbon number of 6 (i.e., hexose) reside in that all the monosaccharides are rearranged from the structural point of view (structural expression of knowledge) and an entire ring image of the hexose can be confirmed on the basis of production processes and molecular structures (D-type and L-type), that an effective and efficient approach can be selected for each item of study, that an optimum production pathway can be designed, and that an omitted portion can be predicted.

Figure 43:
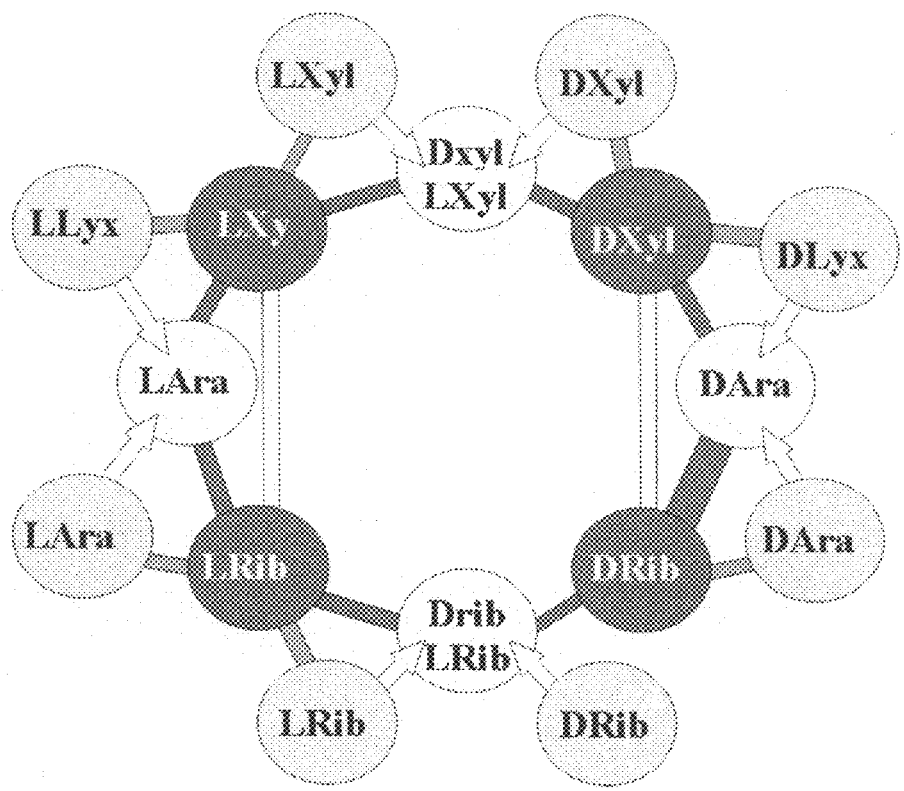
FIG. 43 shows Izumoring of C5, in a medium area of FIG. 41, for more detailed explanation.

As shown in a middle area of FIG. 41 and FIG. 43, the Izumoring of the monosaccharides having the carbon number of 5 (i.e., pentose) is a smaller ring than the Izumoring of the monosaccharides having the carbon number of 6. As in the Izumoring of C6, however, the Izumoring of C5 includes all of 8 kinds of aldose, 4 kinds of ketose, and 4 kinds of sugar alcohols, and these monosaccharides are all linked with each other through enzyme reactions. A different point is that all the monosaccharides can be interconnected in the ring form through only oxidizing/reducing reactions and isomerizing reactions. On the other hand, it is understood that a more efficient production pathway can be designed by using DTE. As seen from FIG. 43, in particular, the Izumoring of C5 is featured in that the monosaccharides contained in the Izumoring of C5 are symmetrically arranged in the left and right direction, while all the monosaccharides contained in the Izumoring of C6 are arranged in a point symmetric way. Since all kinds of pentose are interconnected through enzyme reactions, the Izumoring of C5 has the same useful meanings as those of the Izumoring of C6, namely the meanings that all the kinds of pentose are rearranged from the structural point of view (structural expression of knowledge) and an entire ring image of the pentose can be confirmed, that an effective and efficient approach can be selected for each item of study, that an optimum production pathway can be designed, and that an omitted portion can be predicted.

As shown in an upper area of FIG. 41, the Izumoring of the monosaccharides having the carbon number of 4 (i.e., tetrose) has such a feature that the ring is not completed because of characteristics in structure of tetrose. In other words, the Izumoring of C4 has a similar structure to that of an upper half of the Izumoring of C5. As in the Izumorings of C5 and C6, all kinds of tetrose in the Izumoring of C4 are also linked with one another through only oxidizing/reducing reactions and isomerizing reactions. Because DTE does not react with ketose having the carbon number of 4, any reactions between different kinds of ketose are not yet found up to now. However, the presence of novel epimerase is predicted and researches on the novel epimerase are under continuation at present. As a whole, the monosaccharides contained in the Izumoring of C4 are symmetrically arranged in the left and right direction as in the Izumoring of C5, and includes all of 4 kinds of aldose, 2 kinds of ketose, and 3 kinds of sugar alcohols. Thus, the Izumoring of C4 also has the same useful meanings as those of the Izumorings of C5 and C6.

D-glucose in the Izumoring of C6 is linked with D-arabitol in the Izumoring of C5 and erythritol in the Izumoring of C4. Those linking lines indicate that D-arabitol and erythritol can be produced from D-glucose by using the fermentation method. In other words, the Izumoring of C6, the Izumoring of C5 and the Izumoring of C4 are interconnected. In addition to those two conversion reactions from D-glucose into D-arabitol and erythritol, other linkages between the Izumoring of C6 and the Izumorings of C5, C4 are also possible by using the fermentation method. For example, D-ribose can be produced from D-glucose. Thus, since all the monosaccharides (aldose, ketose and sugar alcohols) having the carbon numbers of 4, 5 and 6 are interconnected through those three Izumorings, it is possible to clearly confirm the location of each monosaccharide in the entire linkage of all the monosaccharides.

It is clearly confirmed, for example, that the most famous xylitol can be easily produced by reducing D-xylose which is producible from wood as resources not utilized. If a particular monosaccharide is obtained in large amount with a biological reaction, it is possible to easily find a possibility of conversion from such a particular monosaccharide as a start material into a new monosaccharide. Stated another way, since positions of all the monosaccharides as start materials can be surely confirmed from the entire ring image, it is possible to design a useful utilization method. Particularly, a utilization method can be easily estimated when any monosaccharide is available from wastes or byproducts. The effectiveness of the linkage map is obtained not only in production of rare saccharides, but also in studies for researching the physiological activity of the rare saccharides. For example, when some rare saccharide is found as having the physiological activity, the location of the relevant rare saccharide in the linkage map shown in FIG. 41 is confirmed. Then, by comparing the physiological activity of the relevant rare saccharide with that of another rare saccharide having a similar structure or by studying the physiological activities of rare saccharides having the structural mirror-image relationship between them, a valuable aid is obtained in estimating the mechanism of the physiological activity from the molecular structure. Further, by analyzing the physiological functions of the rare saccharides and accumulating the analyzed results on the Izumoring, it is expected that resulting data is greatly valuable in comprehensively understanding the whole of monosaccharides from the viewpoints of "structures of the monosaccharides", "production methods of the monosaccharides", and "physiological functions of the monosaccharides" as compared with simple enumerative understanding that has been prevail in the past.

Among the rare saccharides, two ones that are mass-producible at present, i.e., D-allose and D-psicose, will be described below.

D-allose (D-allohexose) is a D-isomer of allose classified as aldose (aldohexose), and it is hexose ($C_6H_{12}O_6$) having the melting point of 178° C.

As methods for producing D-allose, there are known a method of reducing D-allonic acid lactone with sodium amalgam, and a method of synthesizing D-allose from D-psicose by using L-rhamnose•isomerase, as described in Shakkawat, Hossain, Bhuiyan, et al. "Journal of Fermentation and Bioengineering", Vol. 85, pp. 539-541 (1998).

Recently, a method of producing D-allose from D-psicose by causing D-xylose•isomerase to act on a solution containing D-psicose is invented as disclosed in Japanese Patent Laid-Open No. 2002-17392.

D-allose used as, e.g., cancer-cell proliferation inhibitory substance according to the present invention can be obtained by using any of the above-described methods and other suitable methods. With the production method disclosed in Japanese Patent Laid-Open No. 2002-17392, mass production is expected and therefore D-allose is expected to be more easily available. However, the known production methods are all not yet completely satisfiable with regards to recovery through separation of D-allose, and still require uneconomical work from the viewpoint of industrial production. For the purpose of overcoming the drawback, i.e., "a process requiring maximum energy", in the prior art regarding recovery through separation of D-allose, namely providing a method of separating and recovering D-allose with high efficiency, and of providing a technically feasible continuous production method with regards to production of high-purity D-allose, a method of fractionating D-allose with a crystallization process and an application of the method to mass production of D-allose are already separately filed for a patent (Japanese Patent Application No. 2003-95828). The filed method of separating and recovering high-purity D-allose is featured in that, when D-allose is recovered from an enzyme reaction product obtained through conversion of a part of D-psicose into D-allose, e.g., a mixed solution of 35% of D-psicose and 15% of D-allose, D-allose is crystallized by utilizing the properties of D-allose being hard to dissolve in ethanol and/or methanol, and a resulting crystal of D-allose is separated. In that method, an enzyme used for converting D-psicose into D-allose through the enzyme reaction is, e.g., "L-rhamnose isomerase". L-rhamnose isomerase is a known enzyme having been reported in the above-cited paper publicized in 1998, and a preferable example of the enzyme is mentioned as being one derived from *Pseudomonas stutzerii*. A germ strain *Pseudomonas stutzerii* LL172a is a known germ described in the above-cited paper and is preserved in Izumori Ken's Laboratory, Biological Resource Food Chemical Faculty, Agricultural Department of Kagawa University (Japan). The same germ strain *Pseudomonas stutzerii* is also available from Institute for Fermentation (Japan). It seems that *Pseudomonas stutzerii* IFO 3773 and *Pseudomonas stutzerii* IFO 13596 have the same activity. L-rhamnose isomerase can be easily obtained from various microbes, and is derivatively produced under the culter condition where L-rhamnose exists. Usually, L-rhamnose isomerase can be obtained by culturing a microbe that has a capability of producing L-rhamnose isomerase. For example, when various kinds of microbes are cultured by using L-rhamnose as a carbon source, L-rhamnose isomerase is produced in germ cells with L-rhamnose serving as a derivative. Using a variant capable of systematically producing the enzyme in large amount is especially advantageous because an expensive carbon source, such as L-rhamnose isomerase, is not required. L-rhamnose isomerase extracted from the cultured germ cells or the germ cells themselves are used. Depending on the purpose of use, L-rhamnose isomerase is not always required to be refined to a high purity level, and it may be in the form of a crude enzyme. A practical example of the crude enzyme is the microbe itself having the L-rhamnose isomerase producing capability, the culture used for culturing the microbe, or the partly refined culture. In the present invention, a reactor capable of operating at a low feed pressure with stability for a continued long period can be constructed by using the enzyme in the form of the fixated enzyme or the fixated germ which is obtained by using a particular fixation method.

With the above-described method of continuously producing high-purity D-allose, it is possible to perform desalination, deionization, enrichment, and crystallization at the same time as separation of D-allose. Thus, the separation process, which has been performed in discrete steps in the past, can be incorporated into a one-step process. As a result, processing in large amount and in short time can be realized.

D-psicose used in the present invention is a D-isomer of psicose classified as ketohexose belonging to rare saccharides, and it is hexose ($C_6H_{12}O_6$). Such D-psicose may be obtained through any means, including extraction from substances existing in the natural world and chemical or biological synthesis. As a relatively easy way, D-psicose can be prepared, for example, by a method using epimerase (see Japanese Patent Laid-Open No. 6-125776). The obtained D-psicose solution can be refined, as required, through steps of, e.g., protein elimination, decoloration and desalination, and can be enriched to a sirup-like D-psicose product. Further, it is possible to easily obtain a standard product with a high purity of 99% or more by fractioning and refining the obtained D-psicose through column chromatography. The thus-obtained D-psicose can be directly utilized as a monosaccharide, and in addition it is expected to be used as a derivative for various saccharides depending on needs.

In the present invention, the term "physiological-activity sensitive cells" means cells that can be treated with the rare saccharide to modify the function of the cells. Those cells are not limited to particular ones so long as the cells develop such an action. A rare saccharide affects those cells so as to modify the function of the cells. Although the physiological activity differs depending on the kinds of rare saccharides, the physiological activity can be predicted by a preliminary experiment using those cells and can be confirmed by a main experiment. Those cells are preferably human cells, but they include cells other than human cells. The cells may be in the form of internal organs of living bodies or cultured cells.

To treat the physiological-activity sensitive cells with the rare saccharide to develop an action to modify the function of the cells, the rare saccharide is caused to act on the cells. Since the rare saccharide used in the present invention is water soluble, there is no limit in the form of treatment. The rare saccharide can be caused to act on the cells by employing any suitable means depending on the purpose of use.

Preferably, the rare saccharide is caused to act on the cells in the form of a substance in which the rare saccharide is an active ingredient. The substance containing the rare saccharide an active ingredient may be in any form.

In the following, D-allose closest as one of aldose to D-fructose in the Izumoring and D-psicose closest as one of ketose to D-fructose in the Izumoring are taken as two representative ones among the rare saccharides, and their physiological activities are discussed below.

First, examples of the physiological activity of D-allose will be explained.

The inventors have found that the rare saccharide in the form of aldose has properties inhibiting production of active oxygen. Therefore, the present invention can provide an active oxygen production inhibitor containing, as an active ingredient, the rare saccharide in the form of aldose.

More specifically, there is data indicating that D-allose protects the ischemia injury of intestinal organs. When a surgical operation for intestinal organs, such as the liver, is performed, a blood flow is always temporarily stopped. This brings the intestinal organs into the ischemia state. When blood is started to flow again after the surgery, active oxygen is produced in large amount from leukocyte at that time, which is considered as one of major causes bringing about the organic injury. The inventors conducted an experiment through the steps of bringing the livers of rats into the ischemia state for a relatively long time, i.e., 90 minutes, and then reperfusing blood to examine the survival rate of the rats after 3 months depending on application or non-application of the rare saccharide. While the survival rate is usually only 30%, it increased to about 70% by perfusing D-allose at 0.2 g/kg before the ischemia. To prove the above result, various kinds of rare saccharides and other saccharides (such as grape sugar) abundant in the natural world at present were examined for an effect against production of active oxygen from leukocyte. As a result of adding those various kinds of saccharides while active oxygen is produced from leukocyte, only D-allose showed a very strong effect of inhibiting the production of active oxygen. This effect is considered to be one factor making D-allose effective in organ protection.

Further, the above-described protective action against the ischemia is also effective against necrosis of the small intestine cells and brain neurons. Neurons are weak particularly against the ischemia, and it is known that hippocampus neurons die out even with the ischemia just for 5 minutes. As a result of bringing the rat brains into the ischemia for 5 minutes, it was confirmed that 80% of the hippocampus neurons died, but 70% of them was alive even after into the ischemia for 5 minutes by perfusing a solution containing D-allose before the ischemia. Such an effect was not confirmed for D-psicose.

In addition, the above-described ischemia protective effect supports the facts that D-allose has a retina ischemia protective effect, is able to remarkably increase the skin-flap survival rate, and has a kidney ischemia protective effect. It has also been confirmed that the brain neuron ischemia protective effect is based on a glutamate secretion inhibitory effect.

The inventors have found that aldohexose (hexose) belonging to the rare saccharides has properties inhibiting proliferation of cancer cells. Therefore, the present invention can provide a cancer-cell proliferation inhibitor containing, as an active ingredient, aldohexose belonging to the rare saccharides. More specifically, the inventors examined an effect of aldohexose against proliferation of cancer cells by using cells in the form of strain derived from human cancer. Although examination results are detailed in Examples described later, cancer cells proliferate more and more when they are put in a laboratory dish and given with plentiful nutrition and oxygen. By adding D-allose to those proliferating cancer cells, it was found that D-allose had an effect of very strongly inhibiting the proliferation of the cancer cells. A similar effect was confirmed for liver-cancer and skin-cancer cells as well. The cancer-cell proliferation inhibitor containing D-allose, as an active ingredient, may be applied through oral administration, an intravenous injection, an arterial injection or a lymphangial injection, or it may be directly applied to a diseased part. Rare saccharides to be contained, as an active ingredient, in the cancer-cell proliferation inhibitor is not limited to D-allose, and any other rare saccharides in the form of aldose having an effect of inhibiting proliferation of cancer cells (i.e., cancer-cell proliferation inhibitory effect) can also be contained, as an active ingredient, in the cancer-cell proliferation inhibitor.

Further, as a result of examining an influence of D-allose upon leukemia cells, the inventors confirmed that D-allose had an effect of inhibiting proliferation of some types of leukemia cells, and then clarified such an influence mechanism of D-allose upon a cell period that the inhibition of cell proliferation prolonged the G2-M stage of the cell period.

Next, examples of the physiological activity of ketohexose will be explained.

Ketohexose belonging to the rare saccharides does not affect saccharide metabolism and can be applied via various pathways, such as oral administration, abdominal administration, and intravenous administration, as a chemokine inhibitor substance, a microglia migration inhibitory substance, an insulin secretion promotive substance, or a cancer-cell proliferation inhibitory substance. As an alternative, ketohexose may be non-orally applied to a focus or the vicinity of a focus. In that case, ketohexose belonging to the rare saccharides can be used solely, or added with an additive not adversely affecting the effect of ketohexose belonging to the rare saccharides, or modified into a derivative, or employed in combination with any other suitable substance (pharmacologically active ingredient).

Embodiments of the present invention will be described in more detail below in connection with various applications one by one.

The inventors have found that ketohexose belonging to the rare saccharides has properties inhibiting secretion of chemokines. Therefore, the present invention can provide a chemokine secretion inhibitor or substance containing, as an active ingredient, ketohexose belonging to the rare saccharides.

Death attributable to arterial sclerosis ranks first in the death causes. Diabetes, hyperlipemia, hyperpiesia, etc. are indicated as dangerous factors causing arterial sclerosis. According to recent reports, analysis at a molecular is in progress for the relationships between those dangerous factors and development of arterial sclerosis. Development of arterial sclerosis is triggered by migration of monocyte toward the blood vessel wall, accumulation of cholesterol in scavenger receptor, and conversion of macrophage into foam cells. It is suggested that various kinds of cytokines and chemokines are related to the progress of arterial sclerosis. In particular, attention is focused on MCP-1 (monocyte chemoattractant protein-1), as one of chemokines (i.e., a cytokine causing cell migration), which is a factor secreted from vascular endothelial cells of an arterial sclerosis focus and is a factor playing as an important role in the progress of arterial sclerosis.

It was clarified that arterial sclerosis was hard to occur in a knockout mouse in which the function of MCP-1 or CCR2 as a receptor of MCP-1 was stopped, and therefore MCP-1 had a primary role in the development of arterial sclerosis.

MCP-1 is secreted upon stimulation by inflammatory cytokines, such as IL-1$\beta$ and TNF-$\alpha$. As a drug for inhibiting production of such cytokines, a pyrazolotriazin derivative drug and nitric oxide (NO) secretion inducer are known and used for preserving internal organs.

Sodium methylpredonisolone succinate (efficacy: adrenocortical hormone drug) is also commercialized as an inflammatory cytokine and chemokine production inhibitor (by Pharmacia K.K., Fuji Pharmaceutical Co., Ltd., UCP Japan Co., Ltd., and Swai Pharmaceutical Co., Ltd.).

On the other hand, as an example of saccharides or derivatives thereof being used as a arterial sclerosis remedy, hexose calcium phosphate (such as glucose calcium phosphate) acting to reduce the cholesterol concentration in the blood is publicized in Japanese Patent Laid-Open No. 63-198630.

Also, a pyrano-pyranone compound acting to inhibit synthesis of collagen is publicized in Japanese Patent Laid-Open No. 10-330268.

However, there are not yet known an MCP-1 secretion inhibitory effect of ketohexose belonging to the rare saccharides and a derivative thereof, and effective inhibition of arterial sclerosis resulting from utilizing that inhibitory effect.

Confirming the MCP-1 secretion inhibitory effect of ketohexose belonging to the rare saccharides in accordance with the present invention contributes to supporting utility of ketohexose belonging to the rare saccharides in remedy of arterial sclerosis and applicability to clinical treatment. In the embodiments described below, a study is first made of an influence of D-psicose, i.e., one of ketohexose belonging to the rare saccharides, upon MCP-1 secretion from vascular endothelial cells. Then, a study is made of an MCP-1 secretion inhibitory effect of of D-psicose under the presence of cytokines stimulating MCP-1 secretion from vascular endothelial cells.

Thus, because ketohexose belonging to the rare saccharides inhibits MCP-1 secretion, there is a possibility that ketohexose is effective in preventing and remedying arterial sclerosis by using it solely or in combination with any other suitable substance (pharmacologically active ingredient). Also, ketohexose belonging to the rare saccharides is expected as a substance for preventing and remedying diabetes, hyperlipemia, hyperpiesia, etc. Furthermore, ketohexose is expected to be used as an inflammatory cytokine and chemokine production inhibitor, an adrenocortical hormone drug, and a substance substituted for an anti-inflammation agent. Additionally, ketohexose is expected to be used as an organ preservative.

D-psicose promotes secretion of insulin. In experiments using rat's pancreas β-cells strain that secretes insulin, when the concentration of D-glucose as a physiologically secreted substance was gradually increased, the secretion of insulin increased depending on the concentration of D-glucose. When the concentration of D-psicose was increased while keeping the concentration of D-glucose zero, a reaction of secreting insulin depending on the concentration of D-psicose was found as with D-glucose. Further, when 11.2 mM of D-glucose was applied, the secretion of insulin was maximized. When D-psicose was added in that state, the secretion of insulin was further promoted at the time when D-psicose was added to a concentration level comparable to that of D-glucose. At that time, insulin was secreted in amount corresponding to the sum of a maximum secretion amount obtained with D-glucose and a maximum secretion amount obtained with D-psicose.

As described above, the physiological activities of the rare saccharides have been found next by next. When the rare saccharide was applied from the outside of cells, there is a possibility that (1) the applied rare saccharide enters the inside of cells through a carrier, (2) it couples with a receptor, or (3) the presence of the rare saccharide changes metabolism within the cells. Regardless of which one of those possible pathways takes place, it is thought that information is transmitted to the nucleus to change DNA transfer in the nucleus, whereupon protein appearance is changed and hence the cell functions are also changed. Judging from an example of insulin secretion promoted by D-psicose, a possibility of the mechanism being different from the known one is high. The action mechanisms of the rare saccharides have hardly been studied in the past. Therefore, studying those action mechanisms requires an approach of comprehensively analyzing information pathways in cells or internal organs treated with the rare saccharides.

As a result of conducting further researches for the insulin secretion promotive effect with the foregoing in mind, the inventors confirmed that the effect of moderately suppressing the blood sugar value by D-psicose was supported by animal (rat) experiments, that D-psicose was effective in reducing the blood sugar value and promoting insulin secretion in the hyperglycemic condition, and that D-psicose hardly caused saccharification of protein.

While examples of the applications to medicines have been described above, it is also known that D-psicose has not only an effect of inhibiting secretion of chemokine MCP-1, which is a factor accelerating arterial sclerosis, from vascular endothelial cells, but also an effect of inhibiting synthesis of adipose in the liver. This means a possibility that D-psicose is useful for preventing arterial sclerosis, etc. Furthermore, other various physiological activities, such as an effect for new creation of blood vessels and an immunity inhibitory effect, are also expected. In addition to medicines, examples of use of the rare saccharides include foods, drinks, particularly functional foods (for preventing fatness, etc.), cosmetics, livestock feed, and agricultural chemicals (such as a plant growth conditioner and plant blight resistance booster).

For the purpose of providing a substance that has an effect of boosting resistance against plant blight and is expected to realize a drastic reduction in amount of agricultural chemicals used, another group of the inventors separately filed for a patent a plant blight resistance booster using a rare saccharide (Japanese Patent Application No. 2003-95826). When a rare saccharide is used as a substance for boosting resistance against plant blight, the following advantages are expected, i.e., (1) an aqueous solution of a rare saccharide at low concentration (100 μg/ml) quickly activates a resistance gene without using a spreader, (2) the rare saccharide exists just in trace amount in the natural world, but it is a "natural substance"; hence dusting power with high safety is obtained, (3) since the rare saccharide does not show a strong sterilizing action against disease germs, there is no need of considering generation of resistant germs, and (4) not only the use of the rare saccharide alone, but also development as a product mixed with a sterilizer are expected.

When the rare saccharide is mixed in foods, drinks, cosmetics and livestock feed, the mixing rate is not limited to a particular value, but it is preferably in the range of 0.01 to 10 weight %. When the rare saccharide is used as medicines, it can be orally administered in the form of, e.g., capsules, powder and tablets. Since the rare saccharide is soluble in water, it can also be administered through an intravenous injection or an intramuscular injection, for example, in addition to oral administration. The dose differs depending on, e.g., a level in progress of diabetes, and the weight, age and gender of a patient. It is therefore desirable that a proper dose is decided depending on the actual condition case by case when used. The dose of the rare saccharide used as medicines is not limited to a particular value, but it is preferably, per 1 kg of patient weight, about 0.01 to 2,000 mg in the case of oral administration, about 0.01 to 1,000 mg in the case of an intravenous injection, and about 0.01 to 1,000 mg in the case of or an intramuscular injection.

Further, the rare saccharide of the present invention exists in trace amount in food materials and has high safety. If the mass-production technique is developed, the rare saccharide of the present invention is also highly valuable from the viewpoint of cost. Note that an acute oral toxic test showed a value of 5,000 mg/kg or more.

The functional food of the present invention is suitable for use in the fields of health foods for preventing particular diseases (e.g., fatness) and of preventive medicines. In the health foods for preventing particular diseases, vitamins, carbon hydrides, colorants, spices, etc., which are usually added to foods, can be mixed in proper amounts, as optional components, in addition to the rare saccharide as an essential component. The foods can take any suitable form, e.g., the liquid or solid form. Alternatively, edibles containing the rare saccharide can be taken as soft capsules prepared by enveloping the contents with gelatin into the form of capsules. The capsule is made of, e.g., a gelatin coating prepared through the steps of adding water to material gelatin for dissolving the latter, and adding a plasticizer (such as glycerin or D-sorbitol) to the gelatin solution.

In the drug of the present invention, the rare saccharide as an active ingredient is used in itself or as a salt allowable in the drug. Further, in the drug, the rare saccharide can be used not only as a solely manufactured drug product, not only as a drug composition that is prepared by adding a carrier or a diluent and is usable from the viewpoint of drug manufacture. Such a drug product or drug composition can be administered orally or not-orally. For example, when the drug product or the drug composition is orally administered as a solid or fluid (including a gel or liquid), they can take the form of tablets, capsules, pills, globules, powder, granules, or gel preparations. Because the exact dose of the drug product or the drug composition changes depending on the intended usage and the treatment time, a proper dose is decided by a doctor or an animal doctor in charge. The dose to be taken or administered can be appropriately adjusted depending on the drug form. The drug in dose per day may be taken once or several times as an oral solid drug, e.g., a tablet, or an oral liquid drug. Alternatively, the drug may be taken as a drug for an infant in the form of syrup, a troche, or a chewable pastille, for example, so that the drug develops an action not only in a local area, but also in the whole of a body with internal use. In that drug form, the dose per day can be taken by mixing ½ to ¹⁄₁₀ of the dose per day in each drug. In such a case, a total dose taken per day may not reach the prescribed dose.

Conversely, if the dose is not excessive from the viewpoint of the drug form, the dose per day may be mixed in one drug to be taken once. When manufacturing the drug, the drug may be mixed with a diluent, a excipient, and other additives, including a filler, an extender, a binder, an disintegrator, a surfactant, a luster, a coating agent, and a gradually releasing agent, which are usually employed in the relevant art. In addition, the drug further contains, as required, a dissolution aid, a buffer, a preservative, a solubilizer, an isotonizing agent, an emulsifier, a dispersant, a viscosity improver, a gelatinizer, a hardener, an absorber, an adhesive, an elasticity improver, an elasticizer, an adsorber, spices, a colorant, a corrigent, an anti-oxidizer, a moisturizer, a light shielder, a luster, and an antistatic agent.

The present invention can provide an endermic liniment utilizing the anti-inflammation effect of the rare saccharide, i.e., an endermic liniment that has an effect of improving and preventing skin roughness or chappy skin and that is practically used as a remedy, a skin external liniment, a cosmetic, etc. In addition to the rare saccharide as an essential component, the endermic liniment of the present invention can be appropriately mixed with, as required, an aqueous component, an oily component, a powdery component, an alcohol, a moisturizer, a viscosity improver, a UV absorber, a skin whitener, an antiseptic, an anti-oxidizer, a surfactant, a perfume, a colorant, various skin nutrients, etc. Further, the endermic liniment of the present invention can contain, as required, sequestering agents such as di-sodium edetate, tri-sodium edetate, sodium citrate, sodium polyphosphate, sodium metaphosphate; various natural medications such as caffeine, tannine, verapamil, a licorice extract, glabridin, and a hot-water extract of Chinese quince fruit; and drugs such as tocopherol acetate, glycyrrhiziric acid, tranexamic acid, and derivatives or salts thereof; and saccharides such as vitamin C, magnesium phosphate ascorbate, glucoside ascorbate, arbutin, koji acid, D-glucose, D-fructose, and trehalose. The endermic liniment of the present invention is not limited to a particular form, and it may be used in any of the forms of an ointment, a cream, a milky liquid, a lotion, a pack, a bath salt, etc., which have been used in the known endermic liniments.

Details of the present invention will be described below in connection with Examples, but the present invention is in no way limited by the Examples given below.

EXAMPLE 1

(Influence of Rare Saccharide Upon Proliferation of Cultured Cells)

Various kinds of rare saccharides were added at a concentration of 50 mM to culture media under the following conditions, and an influence of each rare saccharide upon the progress of proliferation of cancer cell strains was examined.

(1) Target cells to which the rare saccharides were added: Hepatic cancer cells (HepG2), uterine cancer cells (He1a), ovary cancer cells (OVCAR3), and skin keratinocyte (HaCaT) were selected as target cells to which the rare saccharides were added.

(2) Rare saccharides added: In addition to D-allose, glucose and D-altros as rare saccharides belonging to ketose were added, as other comparative saccharides, to the addition target cells. Also, D-fructose was employed as a control.

(3) Experiment method: A number 3,000-5,000 of addition target cells per type were inoculated into a multi-well plastic dish (hereinafter referred to as a "well") having 96 wells, and were cultured for 4 to 5 days in a culture medium supplemented with 5 to 10% of Fetal Bovine Serum (FBS) depending on the cell types. D-Allose, D-glucose and D-altros were each added at concentration of 50 mM to the addition target cells per type. Similarly, D-fructose as a control was added at a concentration of 50 mM. To examine the influence upon the cell proliferation, the cell number was measured in units of 24 hours by using the MTT method described below.

<MTT Method>

①Preparation of reagents: A predetermined amount of MTT (tetrazolium salt) was dissolved in PBS(–) sterilized in an autoclave to obtain an MTT solution through filtering and sterilization. An acidic solution was prepared by adding 50 mL of N,N-dimethylformaldehyde and water to a predetermined amount of (20 g) of SDS, thereby obtaining a 100 mL of solution. About 200 mL of 1 N hydrochloric acid was added to the solution for adjustment of a pH-value to 4.7. The solution was preserved at room temperature and warmed up to 37° C. just before the use.

②Test method: The cells were treated with TEP to prepare a cell suspension liquid. This cell suspension liquid was pipetted in a predetermined cell-density (300 to 52000 cells/well) to each well (96-well plate: 0.1 mL of culture medium per well). The saccharide as a drug was added in a predetermined amount to each well, followed by cultivation for a whole day and night in a $CO_2$ incubator. Then, 0.5 mg/mL of the MTT solution was added and the resulting culture was incubated for 4 hours in the incubator. Thereafter, the culture medium was completely removed. Then, in a room kept at 37° C., an acid solution was added in amount of 0.1 mL/well. The well plate was placed on a micro-plate mixer and shaken at 37° C. for 20 minutes to dissolve a colored substance (namely, to dissolve "formazan" in the acid solution). The absorbance of the liquid was measured at a wavelength of 570 to 600 nm by using a spectrophotometer. After dissolving the colored substance (formazan) in the acid solution, the absorbance can be measured directly by a plate reader.

Figure 1:
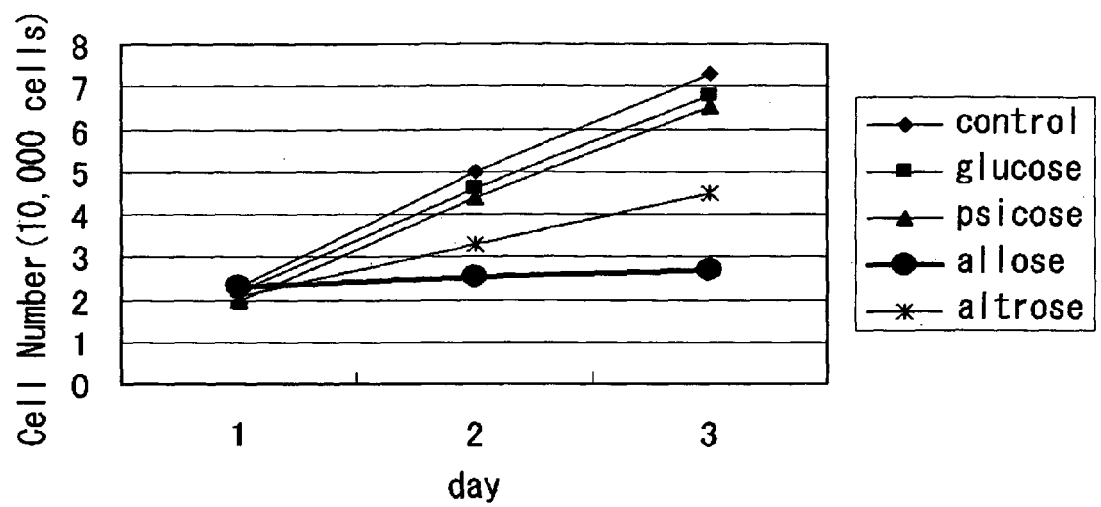
FIG. 1 is a graph showing that D-allose according to the present invention has a proliferation inhibitory effect against hepatic cancer cells (HepG2).

(4) Experiment results: ① Hepatic cancer cells (HepG2) . . . FIG. 1 shows changes over time in the number of the hepatic cancer cells (HepG2). From FIG. 1, it is understood that D-allose strongly inhibited proliferation of the HepG2 cells. D-Altrose was also found as having an inhibitory effect, but its cancer-cell proliferation inhibitory effect was weaker than that of D-allose. The inhibitory effect was hardly found for glucose.

Figure 2:
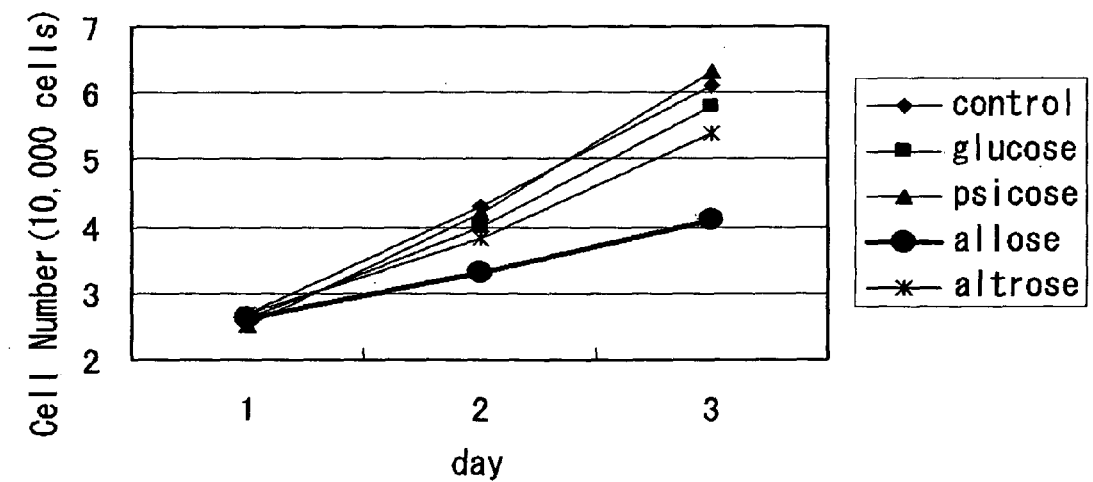
FIG. 2 is a graph showing that D-allose according to the present invention has a proliferation inhibitory effect against uterine cancer cells (Hela).

② Uterine cancer cells (He1a) . . . FIG. 2 shows changes over time in the number of the uterine cancer cells (He1a). It is understood that D-allose strongly inhibited proliferation of the He1a cells.

Figure 3:
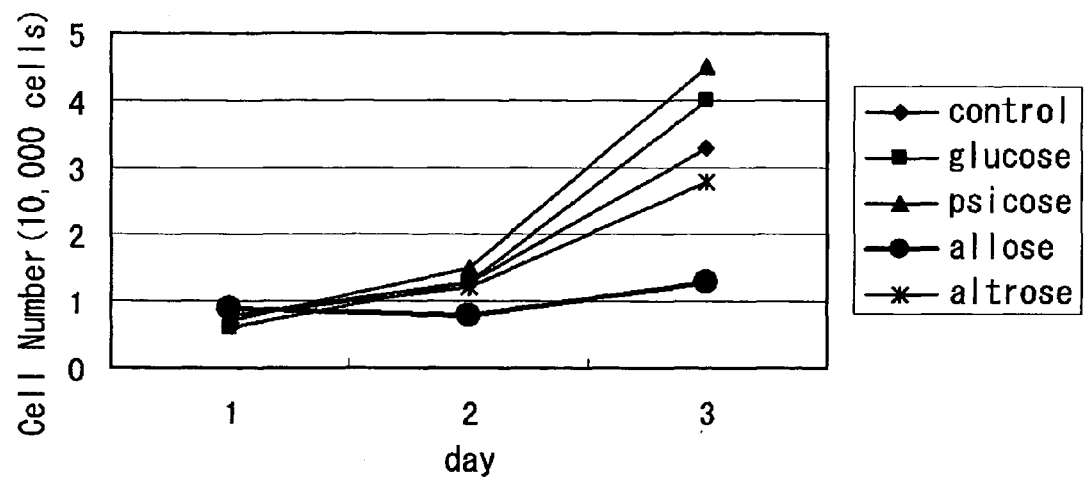
FIG. 3 is a graph showing that D-allose according to the present invention has a proliferation inhibitory effect against ovary cancer cells (OVCAR3).

③ Ovary cancer cells (OVCAR3) . . . FIG. 3 shows changes over time in the number of the ovary cancer cells (OVCAR3). It is understood that D-allose strongly inhibited proliferation of the OVCAR3 cells. D-Altrose was also found as having an inhibitory effect, but its cancer-cell proliferation inhibitory effect was weaker than that of D-allose. Glucose acted so as to promote the proliferation of the cancer cells.

Figure 4:
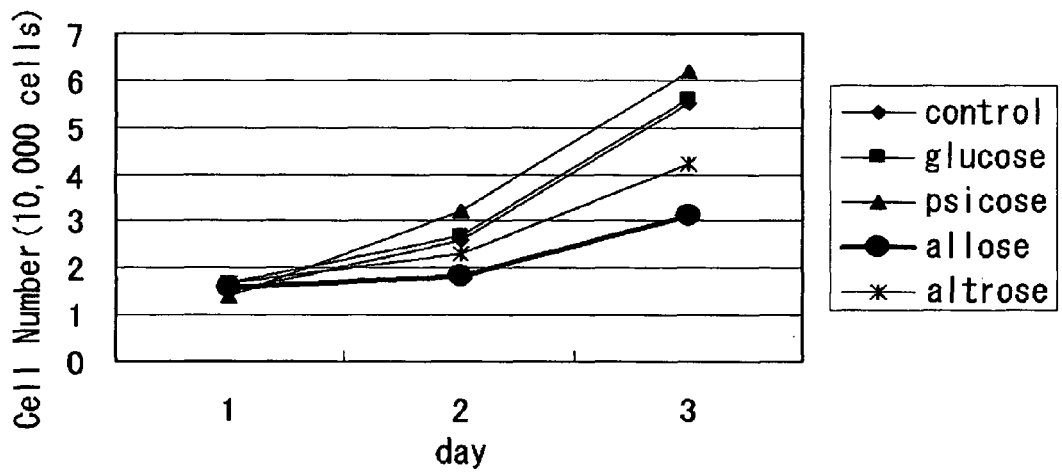
FIG. 4 is a graph showing that D-allose according to the present invention has a proliferation inhibitory effect against skin keratinocyte (HaCaT).

④ Skin keratinocyte (HaCaT) . . . FIG. 4 shows changes over time in the number of the skin keratinocyte (HaCaT). It is understood that D-allose strongly inhibited proliferation of the HaCaT cells. Among the other rare saccharides, D-altrose was found as having an inhibitory effect at a medium level, but its cancer-cell proliferation inhibitory effect was weaker than that of D-allose. As seen from FIGS. 1 to 4, the cancer-cell proliferation inhibitory effect of D-allose differs in strength depending on the cell types. Thus, D-allose as a rare saccharide belonging to aldose has the effect of inhibiting the proliferation of the cancer cells, and it is expected to be effectively used as an anticancer drug. Further, D-alltrose as a rare saccharide belonging to ketose had a cancer-cell proliferation inhibitory effect although the effect was weaker as compared with D-allose. Accordingly, not only D-allose, but also other kinds of rare saccharides belonging to aldose are also expected to be effectively used as anticancer drugs.

EXAMPLE 2

(Concentration Dependency of Cancer-Cell Proliferation Inhibitory Effect of D-allose)

In this Example 2, concentration dependency of the cancer-cell proliferation inhibitory effect of D-allose was examined.

(1) Experiment method: The ovary cancer cells (OVCAR3) were selected as target cells to which a rare saccharide was added, and D-allose as the saccharide was added at concentrations of 1 mM, 5 mM, 10 mM, 20 mM, 50 mM and 100 mM. The experimental conditions, such as the method of culturing the ovary cancer cells (OVCAR3) and the method of measuring the cell number (MTT method), were the same as those in Example 1.

Figure 5:
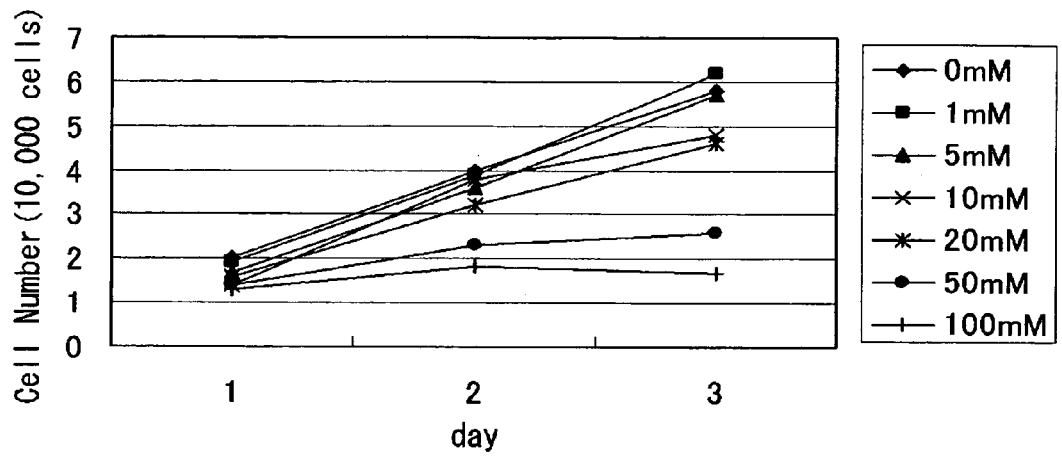
FIG. 5 is a graph showing that D-allose according to the present invention has concentration dependency in cancer cell proliferation inhibitory effect.

(2) Experiment results: FIG. 5 shows changes over time in the number of the ovary cancer cells (OVCAR3) admined with D-allose at the respective concentrations. The cancer-cell proliferation inhibitory effect was first found at 10 mM and then gradually increased in the order of 20 mM, 50 mM and 100 mM. In other words, concentration dependency of the cancer-cell proliferation inhibitory effect of D-allose was confirmed. While the concentration at which the inhibitory effect was first found was 10 mM under the experimental conditions (10% fetal bovine serum) in this Example 2, this effective concentration was the same as that in the other types of cells. Observing the cells, to which D-allose was applied, with a microscope, dead cells hardly existed. This fact was also confirmed by a trypan blue-exclusion assay. From the experiment results in this Example 2, it can be said that D-allose inhibits the cell proliferation, but it has no function of killing the cells.

EXAMPLE 3

(Influence of Rare Saccharide Upon Proliferation of Blood-System Cancer Cell Strain)

This Example 3 is related to a cancer-cell proliferation inhibitory substance containing, as an active ingredient, all-dose belong to the rare saccharides. Although various anti-tumor drugs and anticancer drugs are known, their side effects are problematic in the generalities of cases. Also, at present, consciousness and expectation are increased for drugs or foods (functional foods) targeted on prevention of diseases rather than drugs targeted on remedy of the diseases. In connection with the relationships between saccharides and cancers, there have hitherto been reported that an oligosaccharide acts to keep the intestine in order and therefore it is effective in relieving constipation for protection against a colon cancer. Further, there have recently been publicized reports indicating a cancer inhibitory effect of polysaccharides, such as agaricus, and discussing the relations between sugar chains and metastasis of cancers. However, it is hardly reported that the rare saccharides themselves have the cancer-cell proliferation inhibitory effect. In this Example 3, influences of aldose and ketose belonging to the rare saccharides upon various kinds of cancer cell strains were examined. As a result, it was confirmed that aldose belonging to the rare saccharides had an effect of inhibiting proliferation of the cancer cell strains. The fact that aldose belonging to the rare saccharides, which do not affect the saccharide metabolism, has been confirmed as having the proliferation inhibitory effect against the cancer cell strains means that aldose is expected to be a remedy, a preventive drug, and a proliferation inhibitor against cancers with less side effects. In addition, aldose belonging to the rare saccharides is expected to increase an added value of functional foods. Note that, among various kinds of aldose belonging to the rare saccharides, D-allose was most effective.

(1) Purpose: This Example is intended to comparatively study the cell-strain proliferation inhibitory effects of the rare saccharides.

(2) Method: Total 6 kinds of cell strains, i.e., Myeloid (HL-60, THP-1, KG-1), T-cell (MT-2), and B-Cell (Daudi, KS-1), and 3 kinds of rare saccharides (i.e., D-psicose, D-altrose, and D-allose), were employed. The culture medium and the cells were prepared to be 1 mL in total and $1 \times 10^5$ in number, respectively. Then, the cell number at each of fourth day and seventh day was counted by using a Coulter Counter. Each rare saccharide was added at concentrations of 0.05, 0.5, 5 and 50 mM, while D-glucose was used as a control.

Culture Medium: FBS 10% added RPMI1460
Cultivation Conditions: 37° C., 5% $CO_2$
Cultivation Vessel: FALCON, MULTIWELL, 12 wells
Number of Cultivation Days: 7 days
Saccharides Concentration: 0.05, 0.5, 5, 50 mM (3) Results (FIGS. 6 to 11): Among the cells of 6 strains, an effect was found against the HL60 and Daudi cells, while an apparent influence upon the other types of cells was not found.

Figure 6:
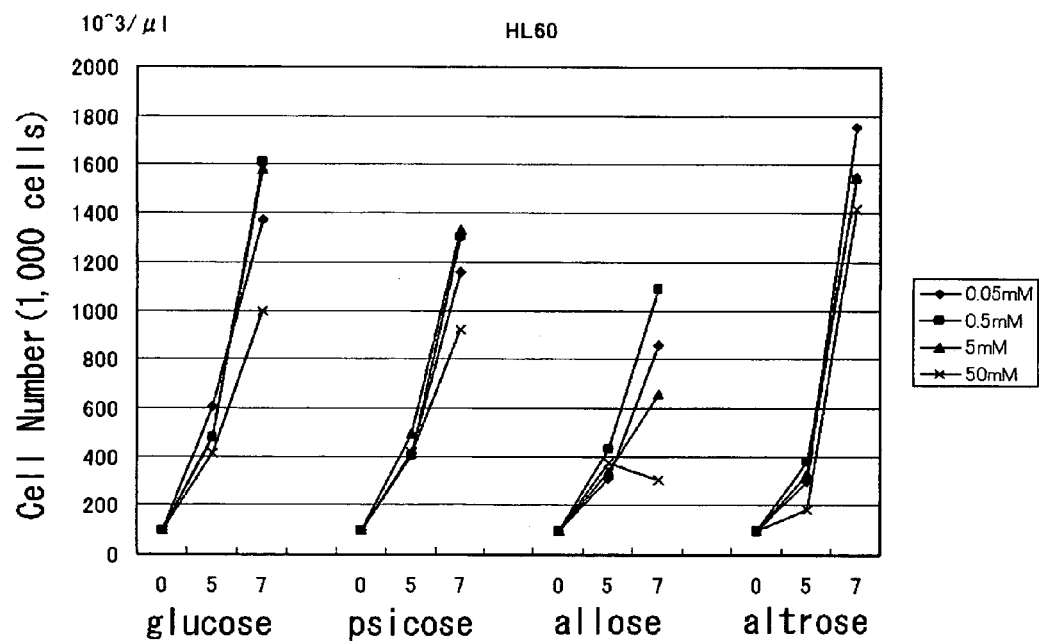
FIG. 6 is a graph showing an HL60 proliferation inhibitory effect of rare saccharides in Example 3.

1) As shown in FIG. 6, psicose and allose showed an inhibitory effect, but altrose showed no effect.
   ① Allose: There was such a tendency that, as the saccharide concentration increased, a stronger cell proliferation inhibitory effect was found at the seventh day; namely, 0.05 mM: 62.6%, 0.5 mM: 67.7%, 5 mM: 41.5%, and 50 mM: 30.7% (the cell number obtained for glucose was assumed to be 100%).
   ② Psicose: The cell proliferation inhibitory effect was substantially constant regardless of the saccharide concentrations; namely, 0.05 mM: 84.7%, 0.5 mM: 80.7%, 5 mM: 84.2%, and 50 mM: 93.6% (the cell number obtained for glucose was assumed to be 100%).

Figure 7:
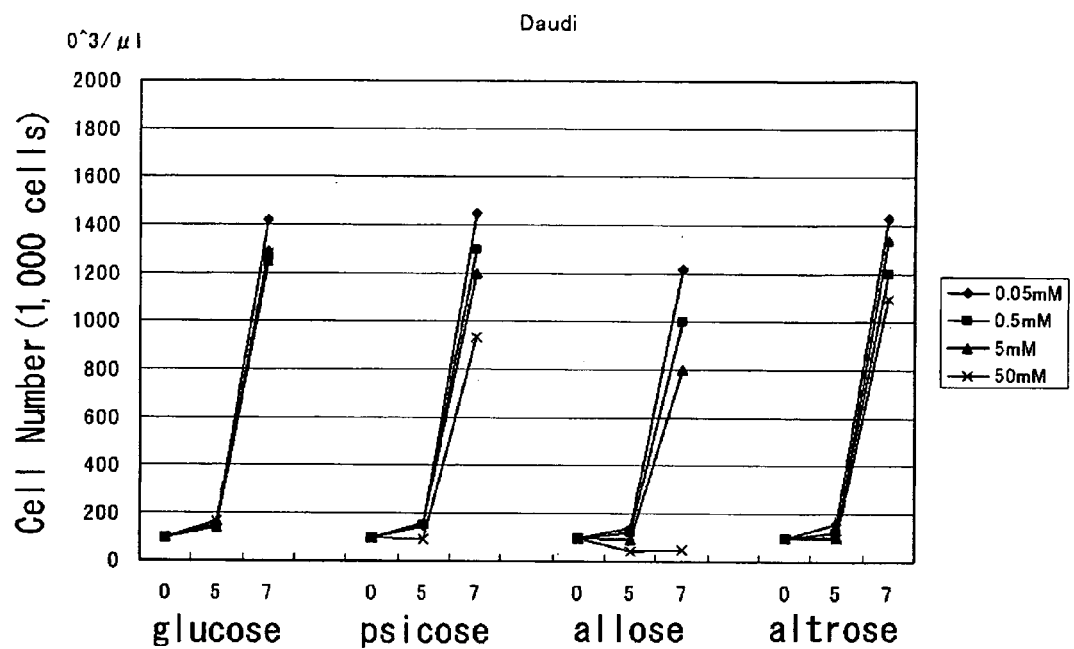
FIG. 7 is a graph showing a Daudi-cell proliferation inhibitory effect of the rare saccharides in Example 3.

2) As shown in FIG. 7, allose showed an inhibitory effect, but psicose and altrose showed no effect.
   ① Allose: There was such a tendency that, as the saccharide concentration increased, a stronger cell proliferation inhibitory effect was found at the seventh day; namely, 0.05 mM: 85.9%, 0.5 mM: 80.6%, 5 mM: 62.2%, and 50 mM: 3.9% (the cell number obtained for glucose was assumed to be 100%).

Figure 8:
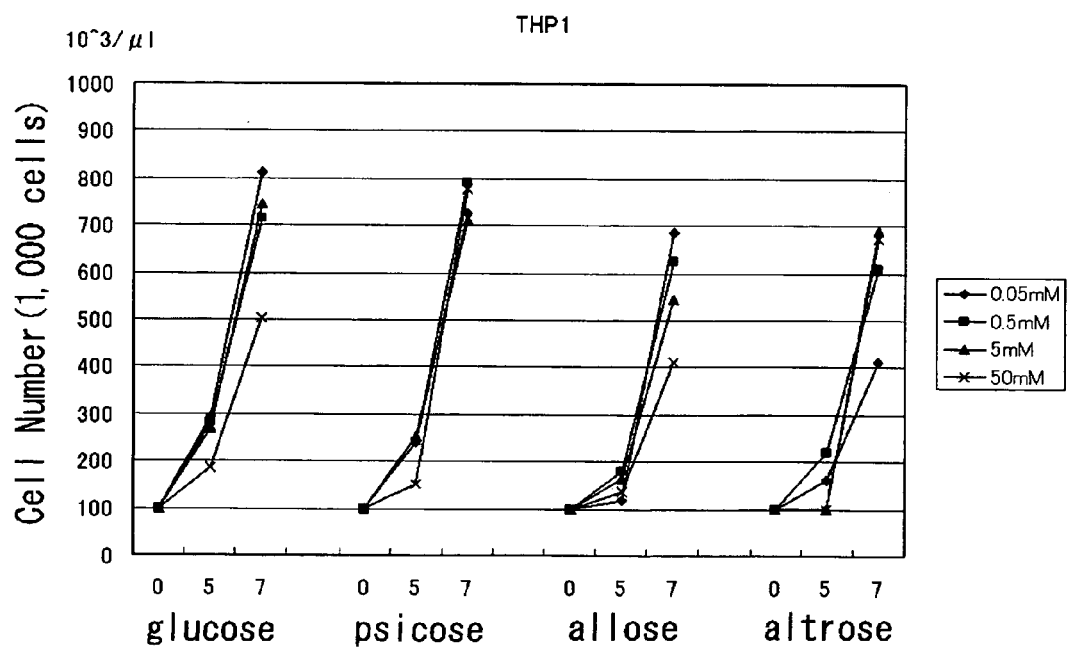
FIG. 8 is a graph showing a THP1 proliferation inhibitory effect of the rare saccharides in Example 3.
Figure 9:
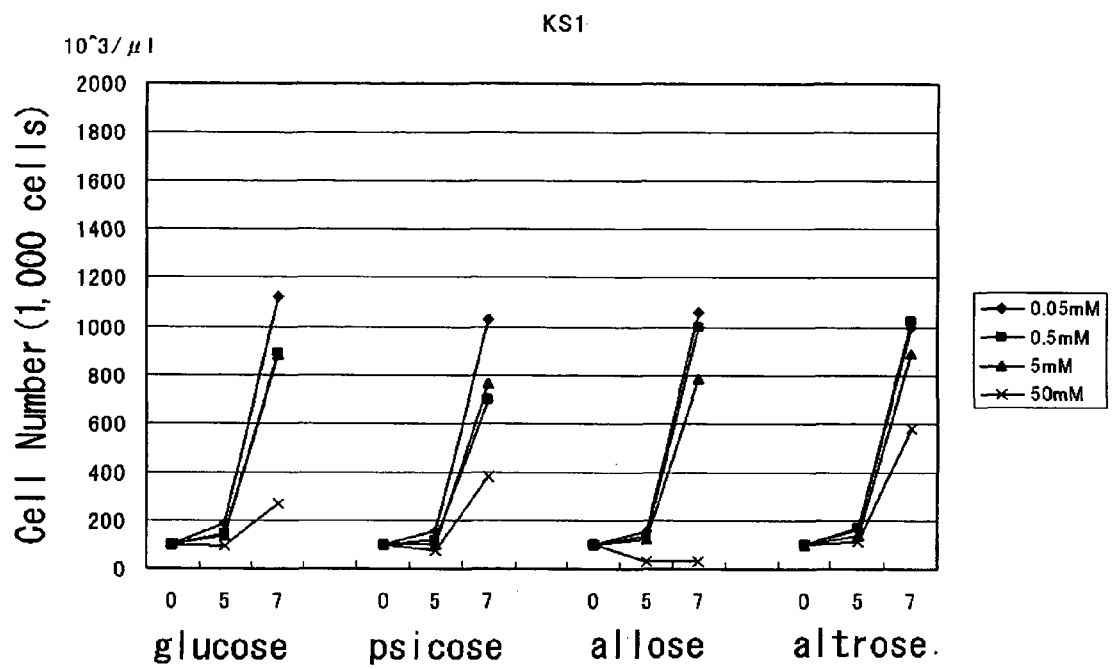
FIG. 9 is a graph showing a KS1 proliferation inhibitory effect of the rare saccharides in Example 3.

3) As shown in FIGS. 8 and 9, allose showed a cell proliferation inhibitory effect at 59 mM, but an apparent inhibitory effect was not shown at the other concentrations and for the other saccharides.

Figure 10:
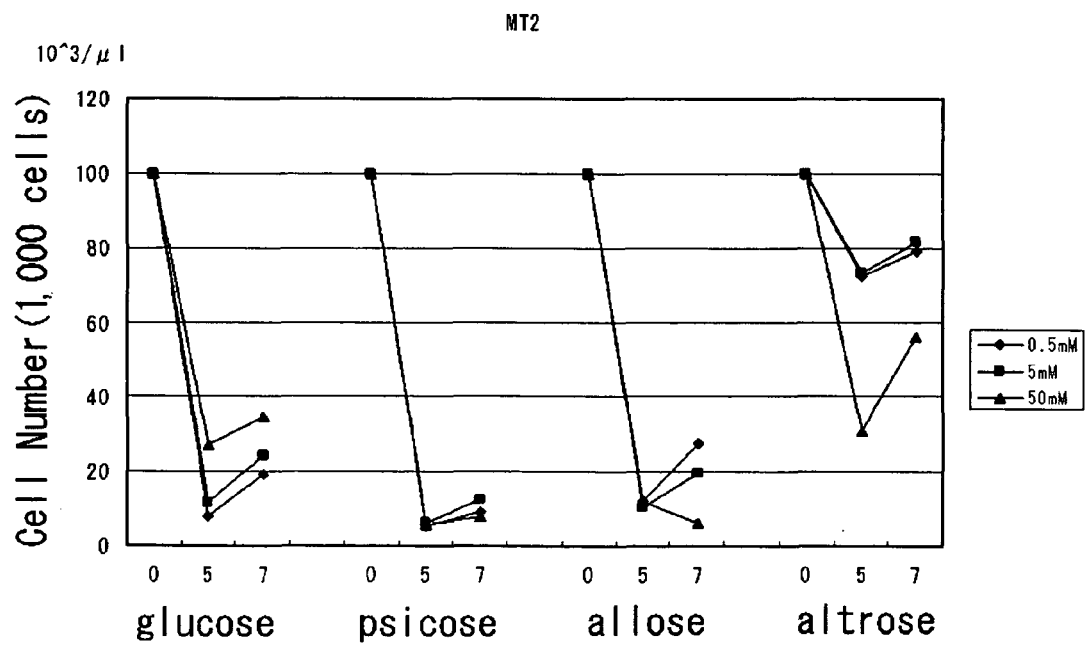
FIG. 10 is a graph showing an MT2 proliferation inhibitory effect of the rare saccharides in Example 3.
Figure 11:
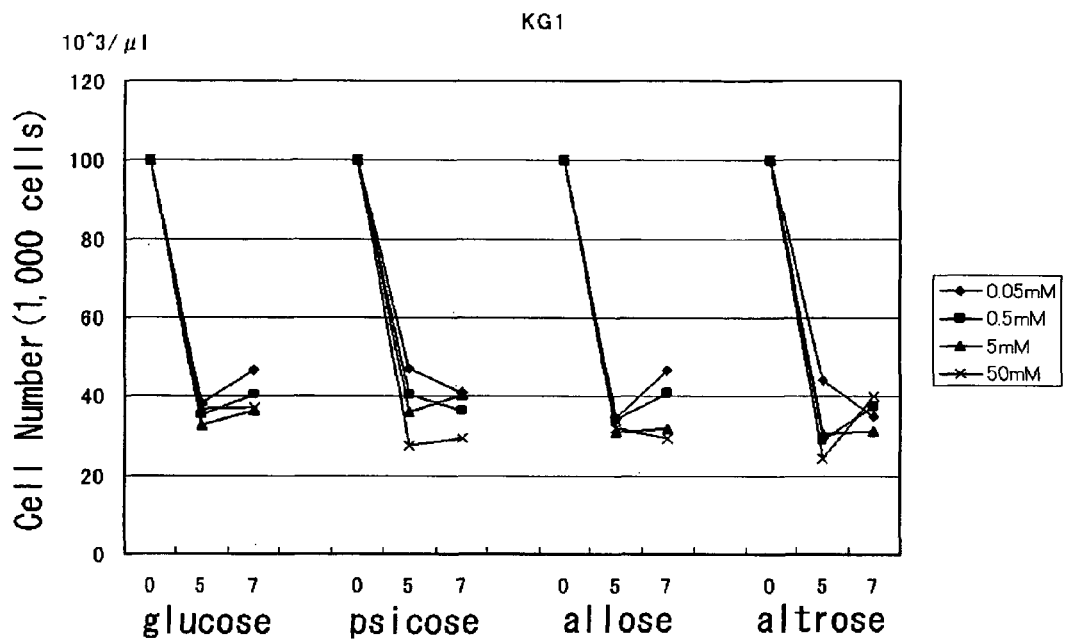
FIG. 11 is a graph showing a KG1 proliferation inhibitory effect of the rare saccharides in Example 3.

4) As shown in FIGS. 10 and 11, an inhibitory effect was shown for all the saccharides and at all the concentrations, including the control. It is therefore deemed that the saccharides in general term have unpeculiar influences upon the target cells.

From the above-described results, D-allose was found as having the inhibitory effect against the four types of cells HL60, Daudi, KS1 and KG1, and it showed the highest inhibitory effect among the rare saccharides used in the experiments. It was also confirmed that the inhibitory effect of D-allose differs depending on the cell types.

EXAMPLE 4

(Influence of D-allose Upon Cell Cycle)

(1) Purpose: As a result of testing various kinds of saccharides, only D-allose inhibited the proliferation of the cancer cells at concentration on the order of mM. In view of that result, though the action mechanism is not yet clarified, an influence of D-allose upon the cell cycle was examined in this Example 4.

(2) Method: The cell cycle was analyzed by using a flow cytometer. Cells used here were OVCAR3 (ovary cancer) cells.

1) The cells were treated with trypsin to prepare a cell suspension liquid.
2) The cells were inaculated into a plastic tissue with a diameter of 100 mm and cultured for 24 hours (overnight) in a $CO_2$ incubator.
3) Two groups of the cells, i.e., one with a rare saccharide (D-allose 50 mM) and the other with no rare saccharides (with D-glucose as a control), were cultured for 3 days.
4) The separated cells were washed twice with PBS(−).
5) After centrifugation, 3 mL of PBS(−) was added and stirred by pipetting.
6) 7 mL of 100% ethanol was added, followed by fixation at 4° C. for 2 hours.
7) The liquid was subjected to centrifugation at 1500 rpm for 5 minutes.
8) The separated cells were washed twice with cold PBS(−).
9) After centrifugation, 200 μg/mL of RNase was added, followed by incubation at 37° C. for 30 minutes.
10) 0.5 mL of PI (propidum iodide) was added, followed by incubation for 15 minutes.
11) The cell number was measured by using a flow cytometer.

Figure 12:
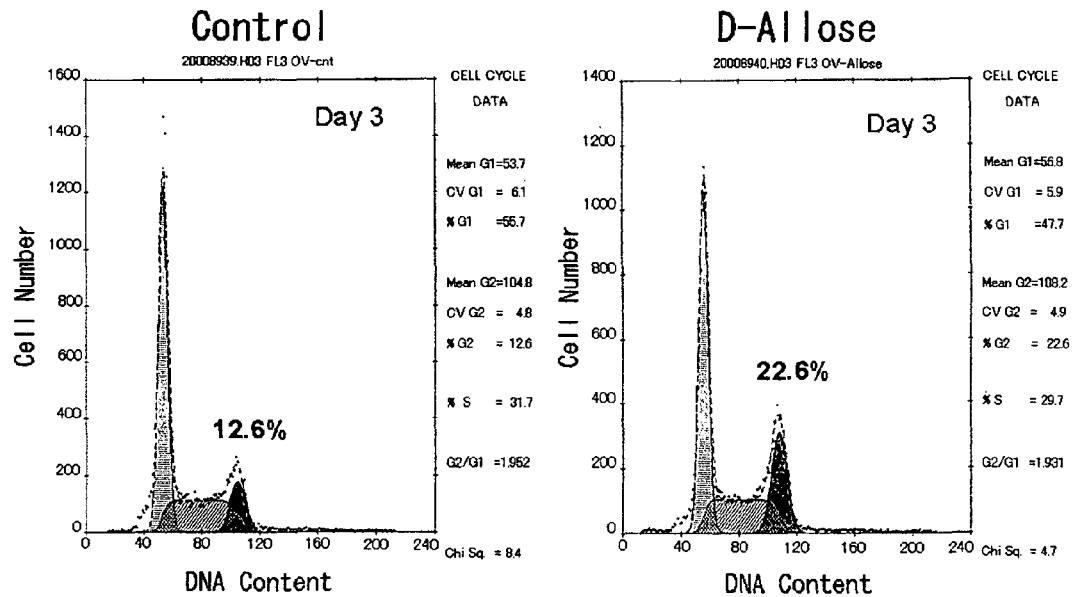
FIG. 12 is a graph showing an influence of D-allose upon the cell cycle resulting from flow cytometry.

(3) Results: For the cells with D-allose, the proportion of the cells in G2-M stage of the cell cycle was 22.6% and it was significantly larger than that in the control, i.e., 12.6% (see FIG. 12).

(4) Reviews: 1) The rare saccharides have been hardly researched in the past, and their physiological functions have also been hardly known at present. Under such situations, the finding that D-allose has the cancer-cell proliferation inhibitory effect means a discovery of a novel function that has been unknown in the past. 2) Although the mechanism is not yet clarified, it was confirmed from the analysis in this Example 4 that D-allose had an effect of delaying G2 stage of the cell cycle.

EXAMPLE 5

(Influences of Rare Saccharides Upon Production of Active Oxygen from Leukocyte)

Influences of various kinds of rare saccharides upon production of active oxygen from leukocyte were examined under the conditions given below. In this Example 5, an effect against the production of active oxygen from leukocyte was examined with LO12 chemiluminescence.

(1) Target leukocyte to which the rare saccharides were added: Rat leukocyte (granulocyte) was used.

(2) Rare saccharides added: In addition to D-allose as a rare saccharide belonging to aldose, D-psicose and D-altros as rare saccharides belonging to ketose and D-tallitol belong to polyol were added as other comparative saccharides. Further, D-glucose and D-fructose were employed as saccharides abundant in the natural world.

(3) Experiment method: ① Changes over time in production of active oxygen from rat leukocyte . . . The time-dependent progress in production of active oxygen caused by adding zymosan particles to rat leukocyte (granulocyte) was examined. Also, the time-dependent progress in production of active oxygen caused under the presence of each of the rare saccharides was examined.

② Influences of rare saccharides upon production of active oxygen . . . By adding the various saccharides to the system for producing active oxygen from leukocyte, the amount of produced active oxygen was measured for each saccharide. The concentration of each of the added rare saccharides was set to 10 mM. Also, the measurement was made under the condition without addition of any saccharides.

③ Effect of rare saccharides upon production of active oxygen . . . The rare saccharides were each added at concentration of 10 mM after the start of phagocytosis and the start of the production of active oxygen subsequent to addition of zymosan to leukocyte.

④ Concentration dependency of active-oxygen production inhibitory effect of D-allose . . . Concentration dependency of the active-oxygen production inhibitory effect of D-allose was examined. D-allose was added at concentration of 0 mM, 5 mM and 10 mM.

Figure 13:
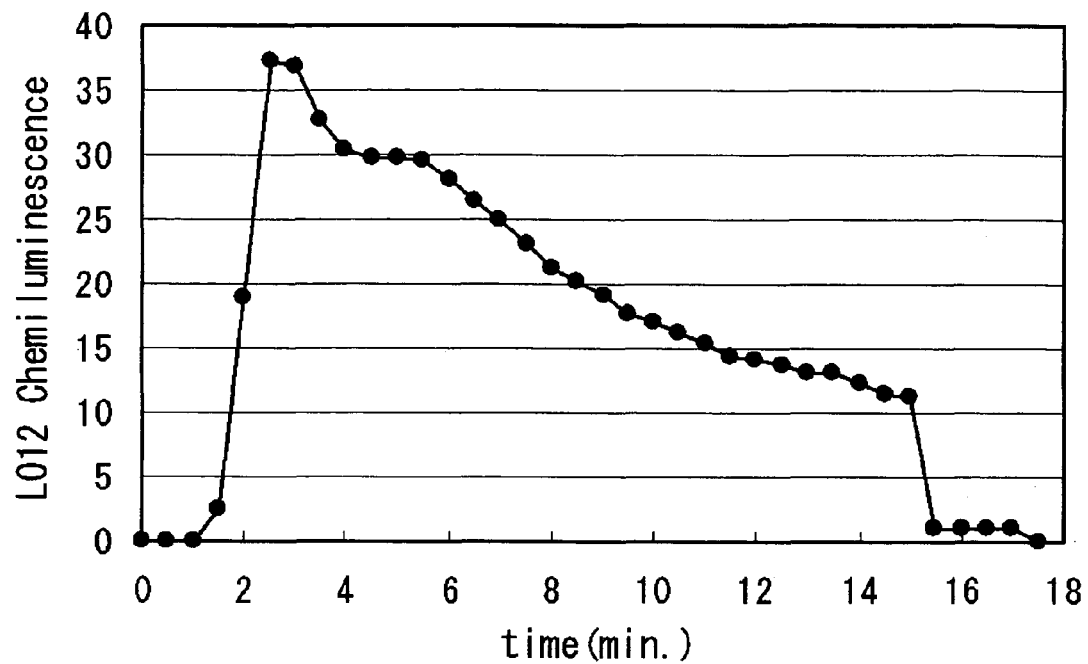
FIG. 13 is a graph showing changes over time in production of active oxygen from leukocyte.

(4) Experiment results: ① Changes over time in production of active oxygen from rat leukocyte . . . FIG. 13 shows the result of examining the time-dependent progress in production of active oxygen caused by adding zymosan particles to rat leukocyte (granulocyte). As seen, the production of active oxygen was maximized in 2 to 3 minutes, and thereafter it gradually decreased. This result was not changed even under the presence of the rare saccharides.

Figure 14:
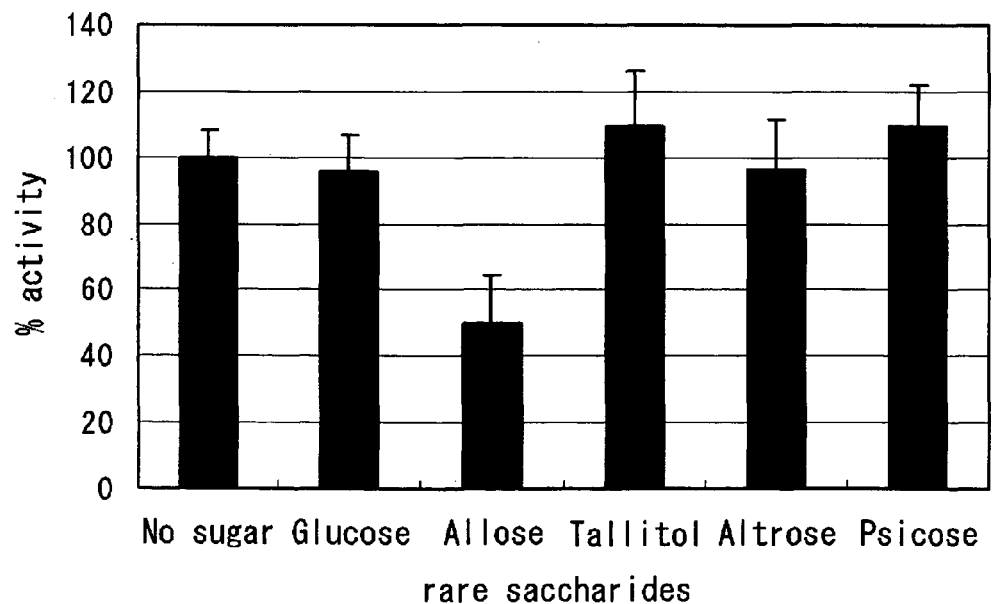
FIG. 14 is a graph showing that D-allose according to the present invention has an effect of inhibiting production of active oxygen by leukocyte.

② Influences of rare saccharides upon production of active oxygen . . . FIG. 14 shows the results of adding the saccharides and measuring the amount of produced active oxygen for each saccharide. The production of active oxygen was inhibited (n=4) only by D-allose. No inhibitory effect was found for the other rare saccharides (D-psicose, D-altrose and D-tallitol), including glucose.

Figure 15:
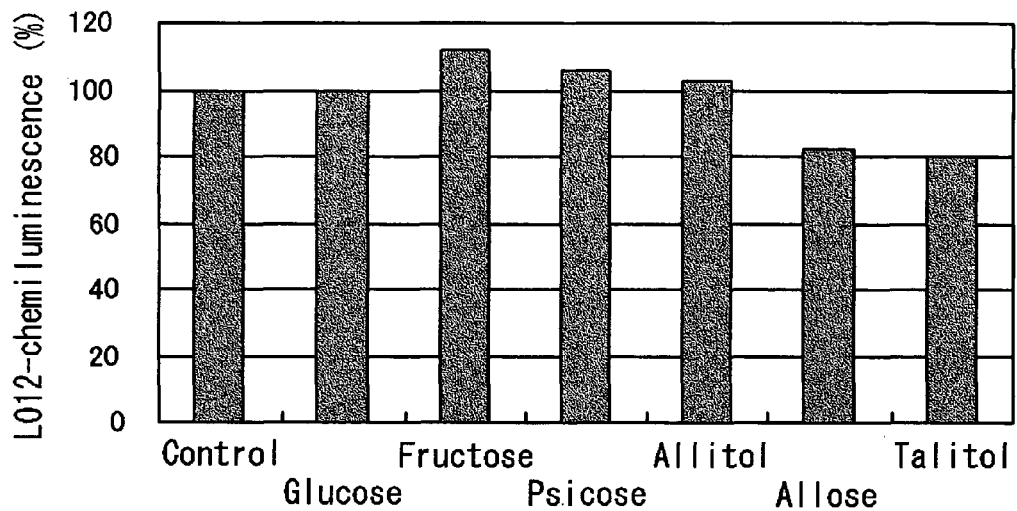
FIG. 15 is a graph showing that various saccharides have no effect of inhibiting active oxygen after start of the production of active oxygen by leukocyte.

③ Effect of rare saccharides upon production of active oxygen . . . FIG. 15 shows the experiment results of adding the rare saccharides after the start of the production of active oxygen. When the rare saccharides were each added at concentration of 10 mM after the start of phagocytosis and the start of production of active oxygen subsequent to addition of zymosan to leukocyte, the inhibitory effect was found for D-allose. It was confirmed from this Example 5 that the time-dependent progress in production of active oxygen was the same regardless of the presence or absence of the rare saccharides. It was also confirmed that, among the rare saccharides examined here, D-allose had a peculiar effect of inhibiting the production of active oxygen (i.e., active-oxygen production inhibitory effect).

Figure 16:
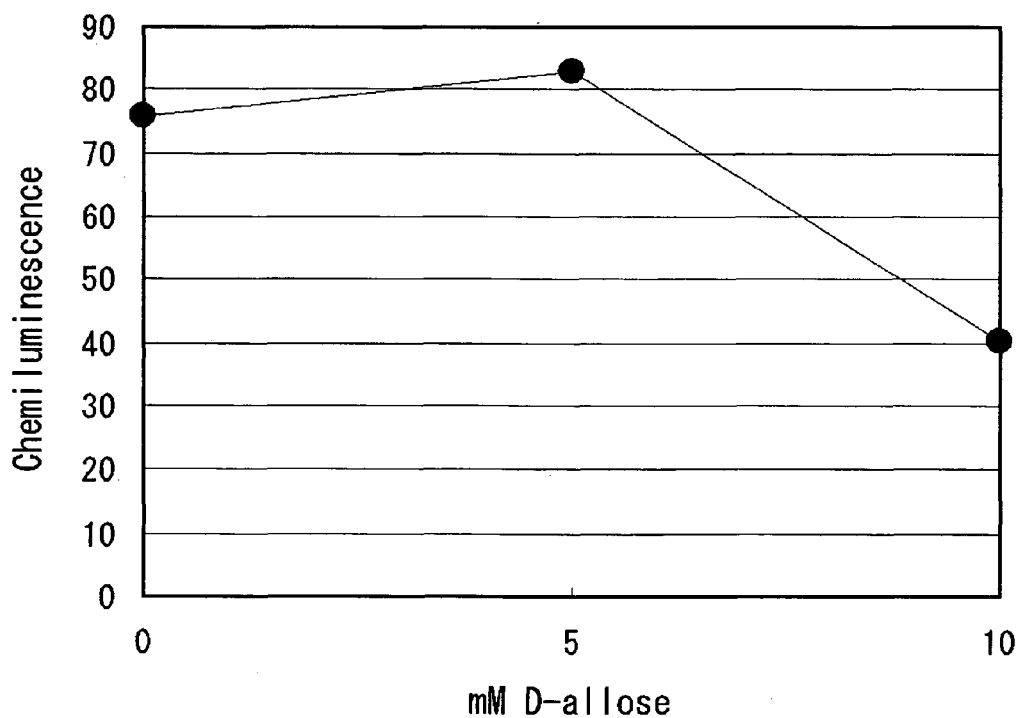
FIG. 16 is a graph showing that D-allose according to the present invention in Example 9 has concentration dependency in active-oxygen production inhibitory effect.

(4) FIG. 16 shows the experiment result of the active-oxygen production inhibitory effect of D-allose at the respective concentrations. As seen from the plotted result, the inhibitory effect of D-allose did not appear at 5 mM, and the inhibitory effect of 50% or more first appeared at 10 mM. Thus, the effective concentration of D-allose was confirmed as being approximately 10 mM. Further, it was confirmed that, from this Example 10 and above Example 5, D-allose had the effect of inhibiting the production of active oxygen. The other kinds of aldose are also expected to have a similar effect, and this point is to be examined in further studies.

The active-oxygen production inhibitory effect is effective against a variety of morbid states and diseases in relation to active oxygen, and therefore expected to be utilized in remedies, functional foods, endermic liniments, etc. in future. For example, diseases for applications as remedies include cranial nerve disorders (such as a temporary brain ischemia fit, cerebral, Parkinsonism, traumatic epilepsy, and spinal cord injury); cardiac and vascular system troubles (such as arterial sclerosis and ischemia miocardosis); respiratory diseases (such as Adult respiratory distress syndrome (ARDS), interstitial pneumonia, byssinosis, virus pneumonia); digestive diseases (such as mucous membrane troubles, liver ischemia-reperfusion injury, jaundice, and pancreatitis); renal diseases (such as glomerulus nephritis, acute renal failure, chronic renal failure, and uremia); diabetes, cancer, ophthalmologic diseases (such as retina denaturation, immature infant retinal trouble, cataract, ophthalmia, and corneal diseases); skin diseases (such as atopic dermatitis, spots, freckles, pigmentation, and skin aging); and collagen disease. As other examples, there is a possibility of application as an organ preservative, a various-organ stem cell preservative, and a spermatozoon/ovum preservative. While the Example employs D-allose as the rare saccharide belonging to aldose, there is also a possibility that other kinds of rare saccharides belonging to aldose, which have the active-oxygen production inhibitory effect, can be similarly used in the applications cited above.

EXAMPLE 6

Figure 17:
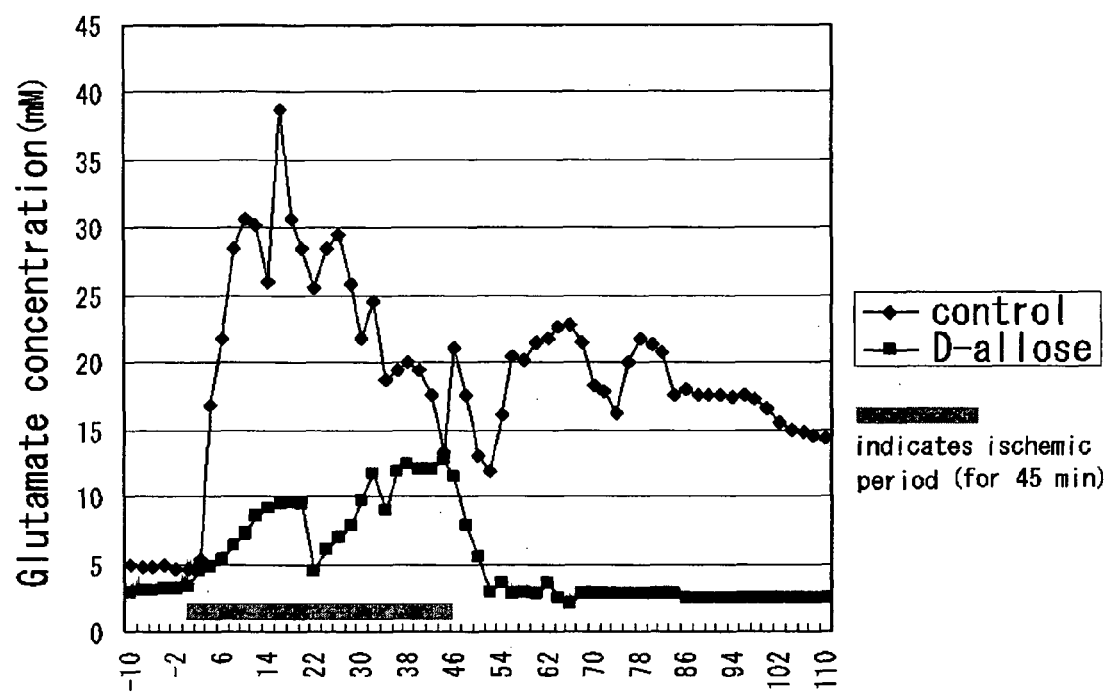
FIG. 17 is a graph showing an effect of D-allose against the retina ischemia-reperfusion injury.

(Effect of Rare Saccharide Against Retina Ischemia-Reperfusion Injury)
(1) Purpose: This Example 6 is intended to study an influence of D-allose upon the retina in a temporary eye ischemia model (rat).
(2) Method: The temporary eye ischemia model was prepared by raising the intraocular pressure up to a level of about 120 mmHg. The model was subjected to ischemia for 45 minutes and then to reperfusion. The concentration of glutamate released in the ischemia-reperfusion process was measured by the microdialysis method.
(3) Results: By administering D-allose (200 mg/kg of body weight) before the ischemia through intravenous injection, as shown in FIG. 17, the glutamate concentration during the ischemia was inhibited in comparison with that in the control (no addition of D-allose), and it was completely inhibited during the reperfusion.
(4) Reviews: In the retina ischemia-reperfusion injury, as in the hippocampus neurons, it is indicated that nurotoxin is generated with release of the glutamate in large amount. The effect of inhibiting the release of the glutamate by D-allose strongly suggests a possibility that D-allose has an effect of protecting retina nerves.

EXAMPLE 7

(Experiments Regarding Skin-Flap Ischemia-Reperfusion Injury Relieving Effect of Rare Saccharide (D-Allose))
(1) Purpose: In the past basic researches, the inventors have tried to find out the mechanisms of skin-flap necrosis after ischemia and reperfusion of island skin flaps and necrosis of distal portions of random pattern skin flaps. As a result, the inventors have clarified that active oxygen is related to the necrosis of island skin flaps after ischemia and reperfusion and the necrosis of distal portions of random pattern skin flaps. Further, it is suggested that active oxygen produced from anginomas and inflammation is also related to the necrosis of island skin flaps after ischemia and reperfusion and the necrosis of distal portions of random pattern skin flaps. In this Example 7, a first purpose is to obtain basic data regarding active-oxygen production inhibitory effects of rare saccharides, and a second purpose is to ensure clinical applications with the view of effectively preventing the necrosis of island skin flaps and random pattern skin flaps. A third purpose is to realize an application as a preservative liquid for long-period preservation of free skin flaps and amputated limbs. (2) Experiment method: 1) A Wistar rat (♂, 7 to 8 weeks, and 300 g or less) was put under anesthesia through abdominal administration of pentobarbital (Nembutal). 2) The abdomen was wholly shaved by a hair clipper. 3) An island skin flap of 3×5 cm was formed in the left abdomen with the left femoral artery and vein serving as blood vessel pedicels. 4) The elevated island skin flap was stitched to the original position by using a 4-0 nylon string. 5) Drugs (0.6 mL per drug) were each administrated in one shot through the right femoral artery and vein by instantaneous injection. The administered drugs were D-allose, glucose (0.2 mg/g), and physiological saline in various concentrations.
6) After waiting for 15 minutes from the administration of each drug, the blood vessel pedicels of both the left femoral artery and vein were clamped. Two vascular clips (60 g for the vein) were used for the clamping.
7) Complete shutoff of blood circulation was confirmed by using a laser Doppler rheometer.
8) After 8 hours, the rats were unclamped. Resumption of blood circulation was also confirmed by using a laser Doppler rheometer.
9) After 1 week, the life or death of the skin flap was determined.
10) An image of the skin flap was taken by a digital camera and input to a computer to calculate a survival area (%) by using area calculation software.
(3) Experiment groups: The following 6 groups were prepared with n=15 in each group.

| | |
|---|---|
| 1) D-allose | 150 mg (0.5 mg/g) |
| 2) D-allose | 60 mg (0.2 mg/g) |
| 3) D-allose | 30 mg (0.1 mg/g) |
| 4) D-allose | 15 mg (0.05 mg/g) |
| 5) D-glucose | 60 mg (0.2 mg/g) |
| 6) physiological saline (control) | |

Figures 20, 21:
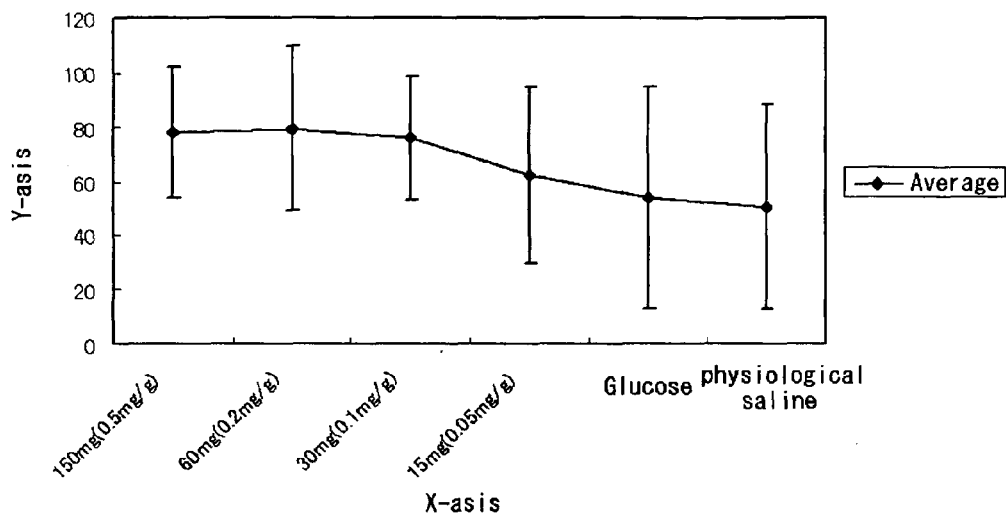
FIG. 20 is a graph showing average values and standard deviations of the data, measured in Example 7, regarding the skin-flap ischemia-reperfusion injury relieving effect of D-allose.
FIG. 21 is a table showing results of a multiple comparison assay, measured in Example 7, regarding the skin-flap ischemia-reperfusion injury relieving effect of D-allose.

(4) Results (FIGS. 17 to 20): FIG. 18 showing all data of the survival areas (%), and FIG. 19 showing results of variance analysis (one-dimensional arrangement). FIG. 20 shows average values and standard deviations of the data, and FIG. 21 shows results of a multiple comparison assay (Fiser's PLSD). In the multiple comparison assay, a significant difference was determined on condition of $p<0.05$.

For the three groups 1), 2) and 3) administrated with D-allose of 30 mg (0.1 mg/g) or more, a statistical significant difference was confirmed with respect to the group 6) administrated with physiological saline. Also, for the two groups 1) and 2), a statistical significant difference was confirmed with respect to the group 5) administrated with glucose. For the group of 4) administrated with D-allose of 15 mg (0.05 mg/g), however, a statistical significant difference was not confirmed with respect to both the group 6) administrated with physiological saline and the group 5) administrated with glucose. Further, the group 5) administrated with glucose did not show a statistical significant difference with respect to the group 6) administrated with physiological saline. It can be therefore said that, unlike D-glucose, D-allose has an effect of extending the skin flap survival area and a dose of 30 mg (0.1 mg/g) or more is required to develop the effect.

(5) Reviews: From the above-described experiments, it was clarified that D-allose had the skin-flap ischemia-reperfusion injury relieving effect. While the mechanism developing that relieving effect requires verification, the inventors deem that D-allose has an anti-oxidation action. To prove such a point, indices of various oxidation stresses must be measured. Stated another way, it is required not only to measure lipid peroxides in skin flap tissues over time by the TBA (thiobarbital) method, but also to measure other parameters such as 4-hydroxy-2-noneal-modified protein (measurement based on immunity dyeing with HNE) and the number of leukocyte (assay from an HE sample).

Clarifying an outline of the mechanism makes it possible to study at what timing the drug should be administered to provide maximum effectiveness. While the drug is administrated to the whole body through the vein in this Example immediately after the elevation of the skin flap (i.e., 15 minutes before clamping the blood vessel pedicels of the skin flap), additional experiments should be continued in which the drug is administrated to the whole body or a local area immediately before clamping the blood vessel pedicels. Further, it is required to study the optimum dose again, and to compare the effect with those of the existing anti-oxidants (such as SOD and allopurinol) when the optimum dose and the most effective administration (timing) are found out. In a future prospect, D-allose is expected to lead to development of syringe medicines and ointments each having the skin flap protective effect. With the development of effective skin flap necrosis preventives, the surgery performance with skin flaps are drastically improved. Furthermore, if preservation of amputated limbs is realized, reunion is no longer performed in an urgent surgery, and the surgery can be performed as a standby surgery at a predetermined time.

(6) References: 1) Ashoori F. Suzuki S, et al: Involvement of lipid peroxidation in necrosis of skin flaps and its suppression by ellagic acid. Plast Reconstr Surg, 94: 1027-1037, 1994.

2) Um S C, Suzuki S. et al: Formation of 4-hydroxy-2-noneal-modified proteins and 3-nitro-L-tyrosine in rat island skin flaps during and after ischemia. Ann Plast Surg, 42: 293-298, 1999.

3) Sato M, Suzuki S, and Muneuchi G.: Change in appearance of Galectin-9 within tissues in skin-flap ischemia-reperfusion injury. Journal of Japan Society of Plastic and Reconstructive Surgery, 22: 428-433, 2002.

4) Yagi K, A simple fluorometric assay for lipid peroxide in blood plasma. Blochem Med. 15: 212-216, 1976

5) Ohkawa H, Ohishi S, Yagi K: Assay for lipid peroxides in animal tissues by thibarbituric acid reaction. Anal Biochem, 95: 351-358, 1979

EXAMPLE 8

(Effect of Rare Saccharides Against Rat Renal Ischemia-Reperfusion Injury)

(1) Purpose: For example, in a surgery accompanying a shock and renal ischemia, an acute renal failure is one of serious complications which may adversely affect the progress after the surgery, including protection of life. In the past, effectiveness of ischemic preconditioning and various medicines has been studied for a renal ischemic injury. In this Example 8, an effect of rare saccharides against the renal ischemic injury by using a rat renal ischemia-reperfusion injury model.

(2) Method:

Target . . . Male rat with weight of about 300 g.

Experiment method . . . The renal ischemia model was prepared after putting the rat under anesthesia with Nembutal.

Renal ischemia . . . After picking up the right kidney, the left renal blood vessel was clamped for 45 minutes.

Drugs used . . . D-allose and D-psicose (400 mg/kg per drug) were administrated into the vein 30 minutes before clamping for renal ischemia.

Measurement item . . . An influence of each drug upon appearance of a trouble factor, i.e., cytokine-included neutrophil chemoattractant (CINC)-1mRNA, was measured (after reperfusion for 2 hours).

Figure 22:
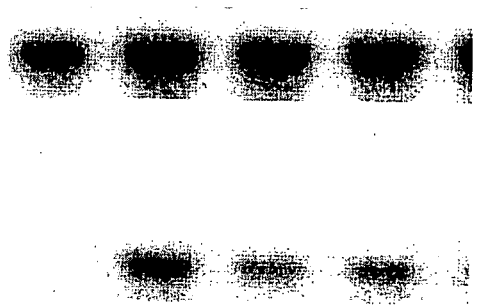
FIG. 22 is a photo, instead of a drawing, showing an effect of rare saccharides against the rat renal ischemia-reperfusion injury measured in Example 8, the photo showing results of northern blotting. More specifically, the photo represents an appearance rate of mRNA of CINC-1. As a standard, mRNA of GAPDH (glyceraldehydes 3-phosphate dehydrogenase) was taken and confirmed as being almost constant (upper area of the photo). Then, the appearance rates of mRNA of CINC-1 in various conditions were compared. In the photo, each image represents the kidney before ischemia, after ischemia, in a condition of ischemia after applying D-allose, and in a condition of ischemia after applying D-psicose from the left. As shown, mRNA of CINC-1 did not appear at all before ischemia, but it appeared after ischemia. The appearance rate was suppressed after applying D-allose and D-psicose.

(3) Results (FIG. 22): FIG. 22 shows the results of northern blotting. As seen, the appearance rate of CINC-1mRNA after reperfusion for 2 hours is reduced for both of allose and psicose.

(4) Reviews: This Example 8 shows the results of only one series of preliminary experiments, and hence further experiments are required to study the effect in more detail, including the required concentration, for example. It is also required to study not only the appearance rates of CINC-1 mRNA, but also influences of the rare saccharides upon CINC-1 protein. If the effectiveness of the rare saccharides against the renal ischemic injury, those rare saccharides are expected to lead to development of a new remedy and liquid transfusion drug.

EXAMPLE 9

(Study on Brain Ischemia Protective Effect of Rare Saccharides)

(1) Purpose: It is known that hippocampus neurons are brought to necrosis with temporary brain ischemia. The cause is not yet clarified, and several potential hypotheses are proposed. At present, many researchers are trying to prove those hypotheses. As a result of conducting studies based on this model, the inventors have found that the necrosis of hippocampus neurons is inhibiting by pre-administration of D-allose. Further, the inventors have determined the dose in more detail and have clarified a part of the action mechanism.

(2) Method: The bilateral common carotid artery of a gerbil was shut off for 5 minutes. After 1 week, the gerbil was sacrificed and a sample was prepared in accordance with the ordinary method, followed by hematoxyline eosin dyeing. The survival rate was measured by counting the number of hippocampus neurons while looking at them under a microscope. Experiments were performed on a normal control group, a group subjected to only ischemia, and a group administrated with 200 mg/kg of D-allose or D-psicose before ischemia. It is known that glutamates released in large amount from the neurons with ischemia are toxic to the neurons. Such a point was examined by fixing the gerbil to a brain position fixing device, perfusing a solution, in which oxidase glutamate is dissolved, to the hippocampus through a probe for micro-dialysis, and measuring the glutamate concentration outside the hippocampus neurons. Also, the inventors have clarified the relationship between the metabolism of glucose and the action mechanism of D-allose with ischemia by pre-administrating D-allose and 2-deoxiglucose.

Figure 23:
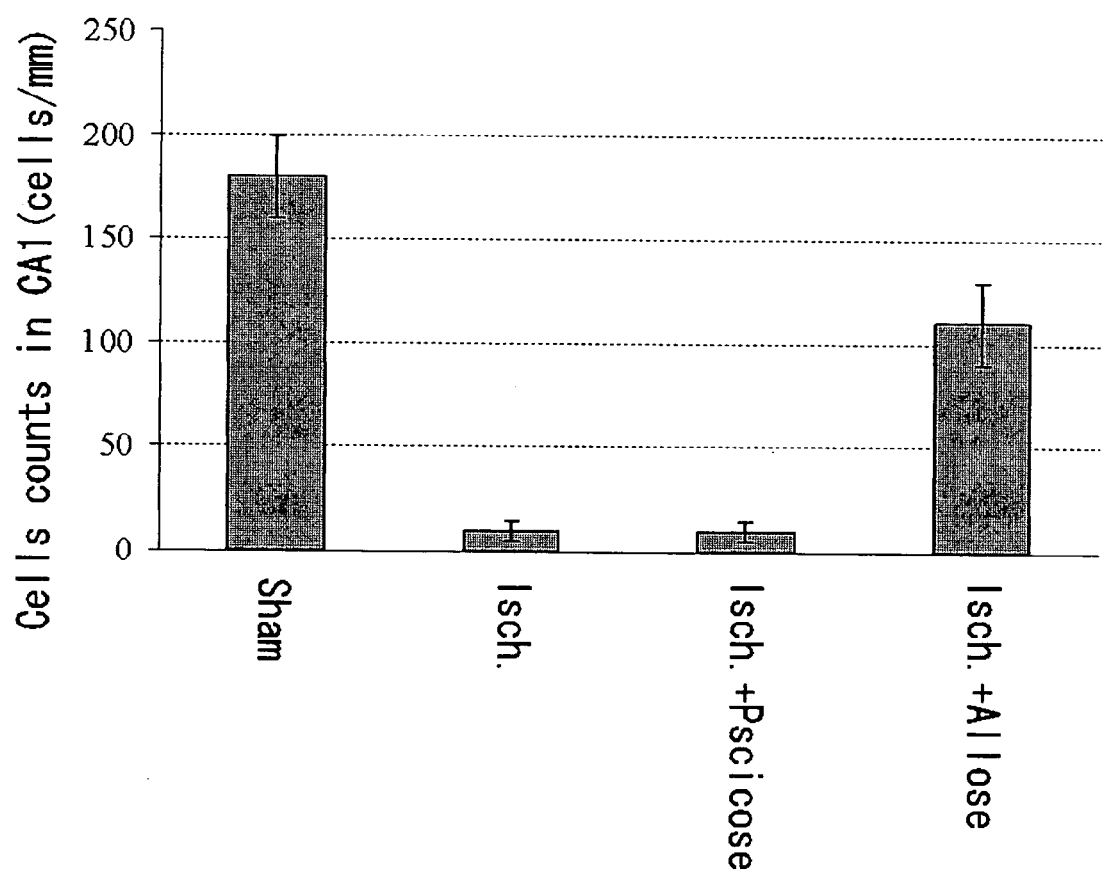
FIG. 23 is a graph showing an effect of rare saccharides for inhibiting necrosis of hippocampus neurons measured in Example 9.
Figure 24:
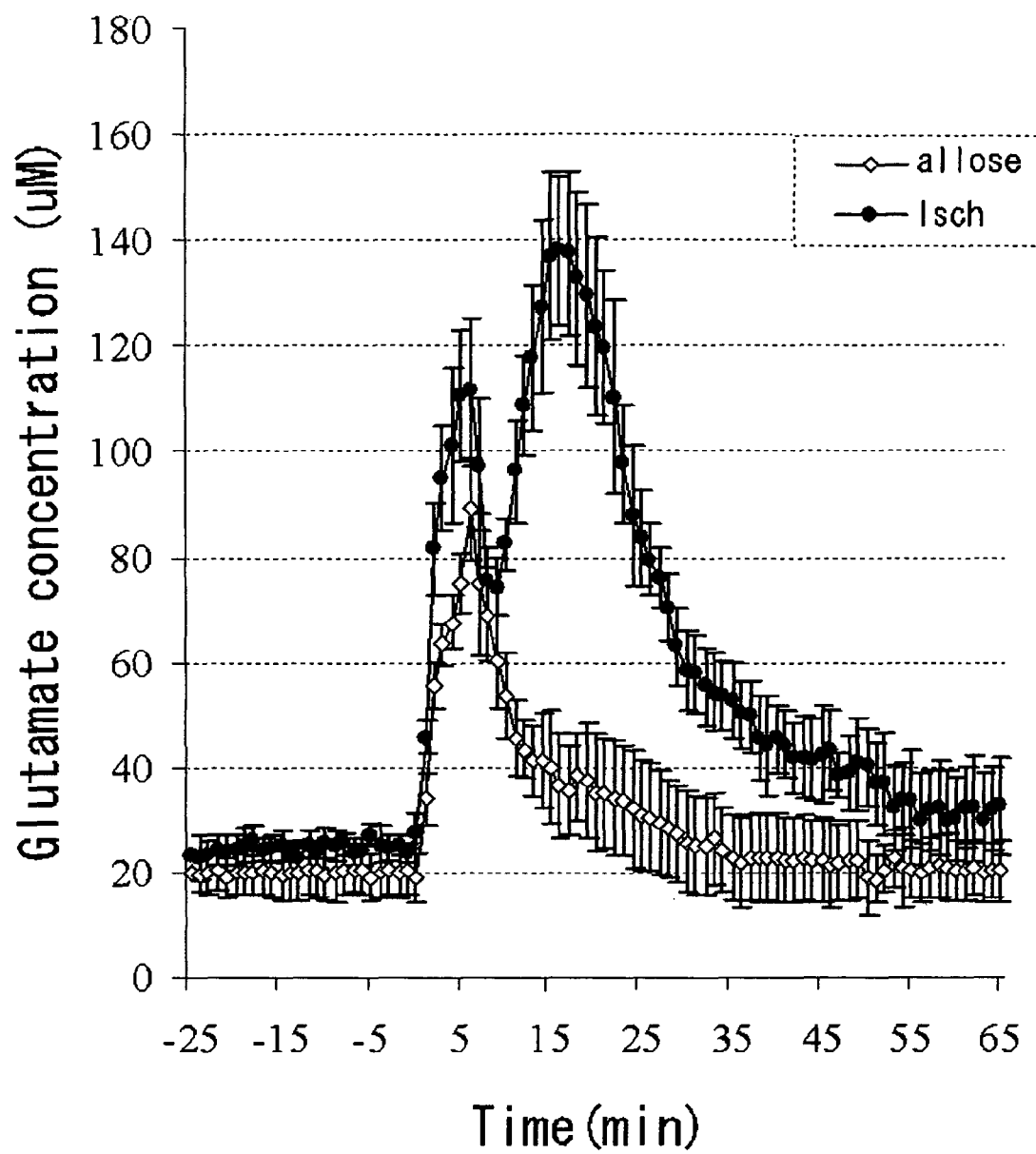
FIG. 24 is a graph showing glutamate release externally of neurons with brain ischemia and a release inhibitory effect of allose measured in Example 9.
Figure 25:
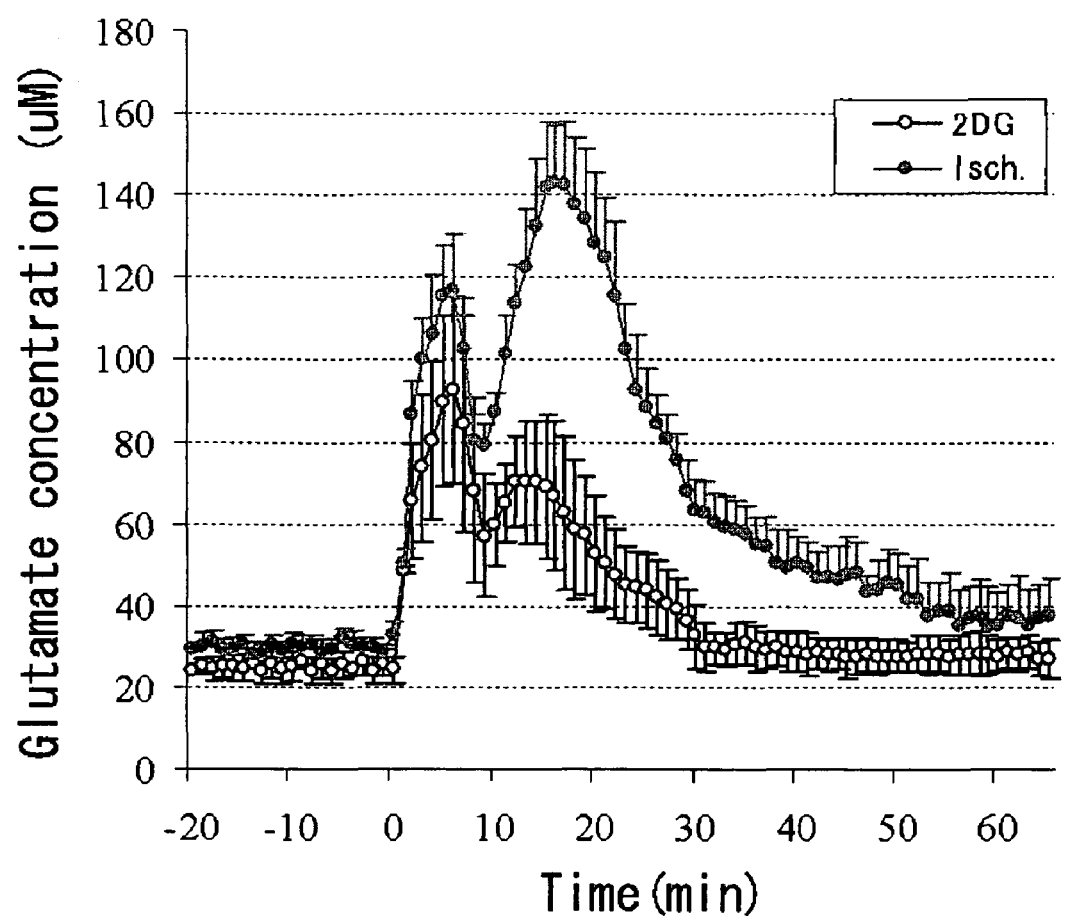
FIG. 25 is a graph showing glutamate release externally of neurons with brain ischemia and a release inhibitory effect of 2-deoxyglucose measured in Example 9.

(3) Results: D-allose significantly inhibited necrosis of the neurons caused by ischemia. However, such an inhibitory effect was not found for D-psicose (FIG. 23). With ischemia, the hippocampus secreted the glutamates in two phases (FIG. 24). A first peak appeared with ischemia, and a second peak appeared with hyperperfusion after the end of ischemia. The hyperperfusion continued for about 1 hour, and it seems that the neurons were damaged during the hyperfusion. The pre-administration of D-allose partly inhibited the first peak, but the inhibition rate was about 25%. On the other hand, the second peak was strongly inhibited at a rate of about 90% the administration of D-allose (FIG. 24). Such an effect was similarly observed with administration of 2-deoxyglucose that was a non-metabolic D-glucose related substance (FIG. 25).

(4) Reviews: It is known that D-glucose is essential to nerve activities and generates cell toxicity depending on excess and deficiency. Also, when strong stresses are exerted and supply of oxygen is shut off as in ischemia, high cell toxicity is generated. This is presumably attributable to cell failures caused by generation of active oxygen. It deems that D-allose inhibits necrosis of the neurons by affecting the metabolism of D-glucose in some way. This point was proved from the result that the similar effect was observed with the administration of non-metabolic 2-deoxyglucose. Meanwhile, a possibility was shown that D-glucose was consumed with brain ischemia in not only neurons, but also in stellate glia cells, and both types of the cells struggled for D-glucose. It is also reported that final products resulting from consumption of D-glucose in the stellate glia cells differ from those in the neurons, and a lactic acid is released under action of an anaerobic metabolic system. Because, though being preliminary data, secretion of a lactic acid during ischemia is actually observed, it deems that D-allose partly acts in the stellate glia cells. Further, there is a possibility that the second peak representing the glutamate release is attributable to active oxygen.

EXAMPLE 10

(Ketohexose's Effect of Inhibiting Secretion of Chemokine MCP-1 Related to Worsening of Arterial Sclerosis)

Human vascular endothelial cells (HUVECs) were cultured under the culture medium condition of (DMEM+10% FBS) in accordance with the ordinary method. HUVECs at concentration of about 70% were pipitted into a 96-well culture dish, and the following experiments were performed.

Figure 26:
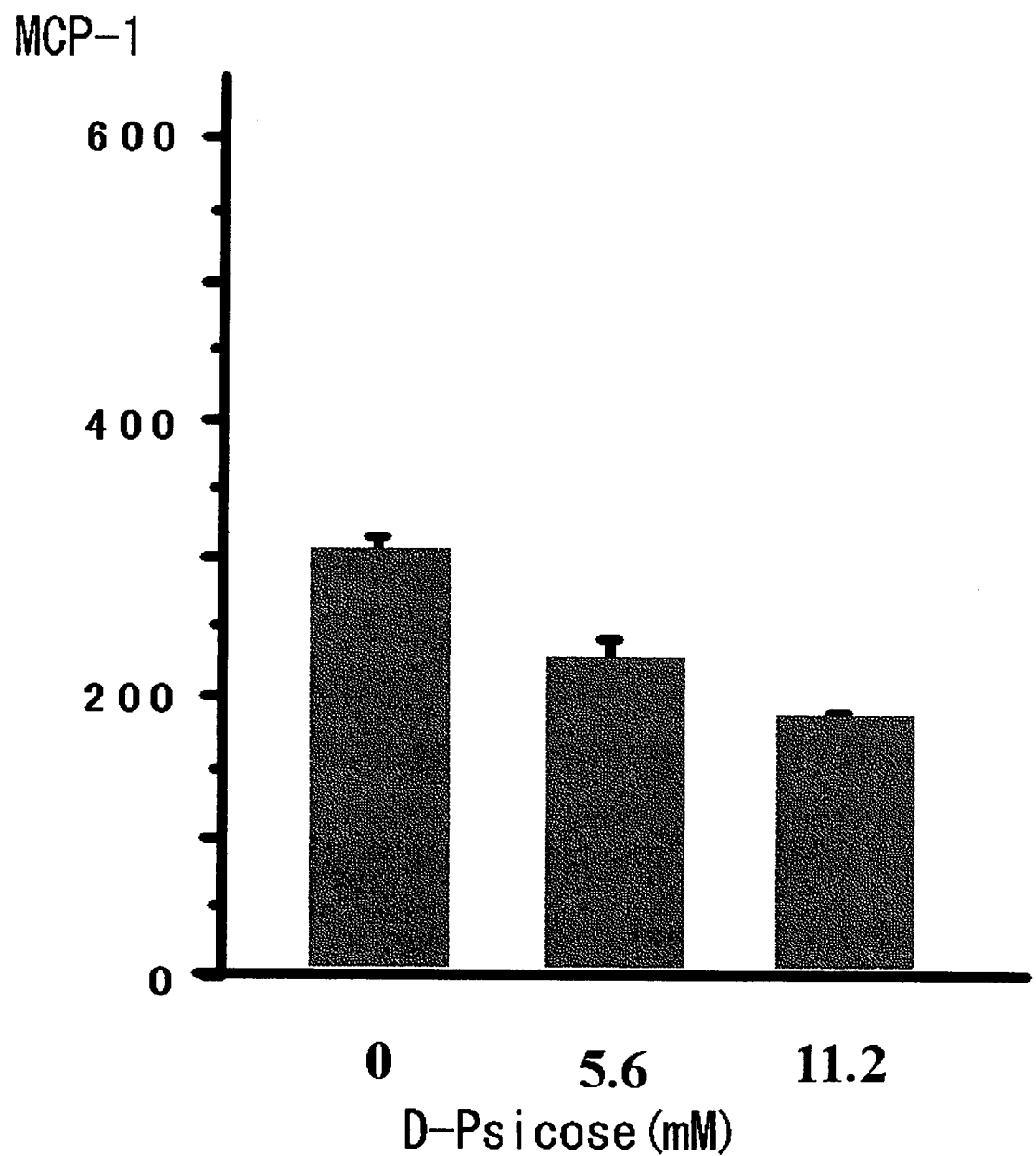
FIG. 26 is a graph, measured in Example 10, showing that D-psicose has a MCP-1 secretion inhibitory effect.

(Experiment 1)
D-psicose was added to the HUVECs culture medium at concentrations of 0 mM, 5.6 mM and 11.2 mM. After cultivation for 24 hours, MCP-1 in the culture medium was measured by using an ELISA (Quantikine, R&D) kit. FIG. 26 shows the measured results.

Figure 27:
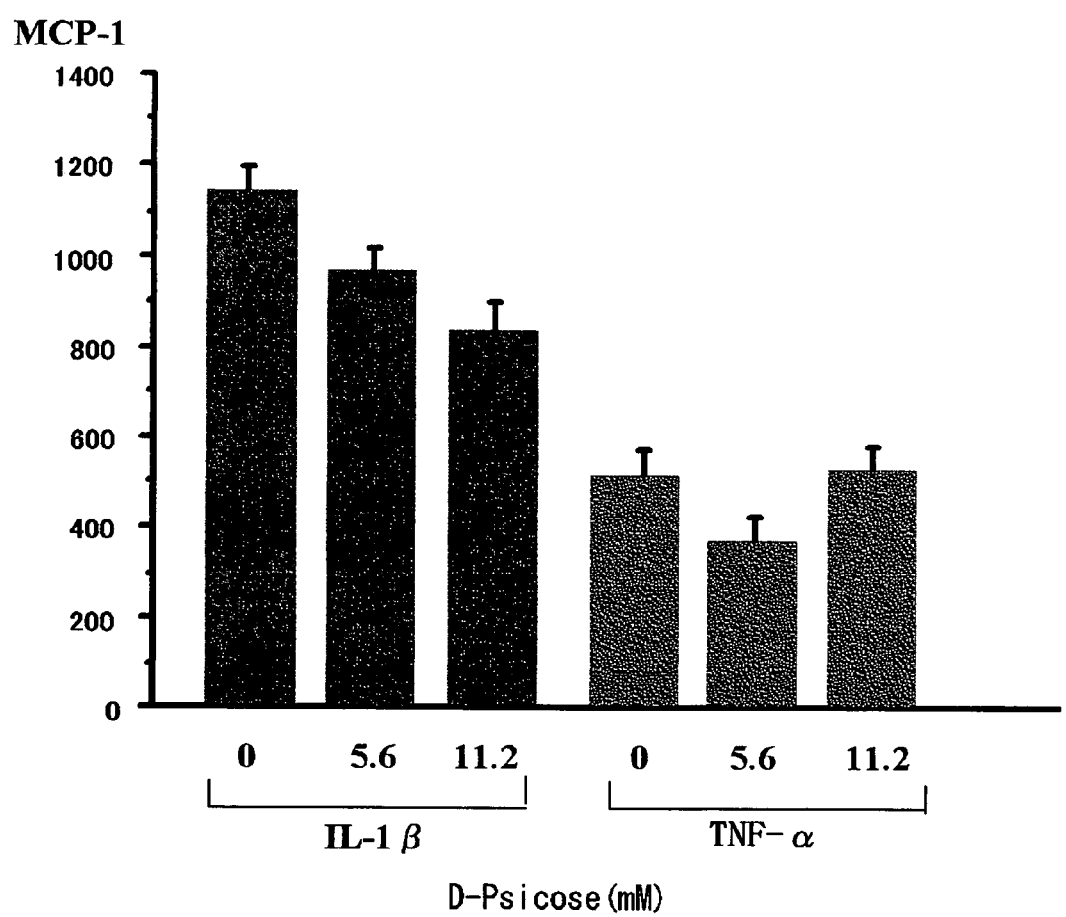
FIG. 27 is a graph, measured in Example 10, showing that D-psicose acts on cytokines stimulating secretion of MCP-1 and inhibits secretion of MCP-1.

(Experiment 2)
HUVECs were pretreated for 1 hour with cytokines acting upon HUVECs and stimulating secretion of MCP-1, i.e., IL-1β (maximum secretion stimulus concentration of 1 ng/mL), and TNF-α (maximum secretion stimulus concentration of 10 ng/mL). Then, D-psicose was added at concentrations of 0 mM, 5.6 mM and 11.2 mM, and after 24-hour cultivation, the MCP-1 concentration in the culture medium was measured by using the ELISA kit. FIG. 27 shows the measured results. From FIG. 26, it is understood that, in relation to basic secretion of MCP-1 in the vascular endothelial cells, D-psicose is able to inhibit the secretion of MCP-1 depending on the concentration. The secretion of MCP-1 in the vascular endothelial cells is stimulated by cytokines (IL-1β, TNF-α) at maximum secretion stimulus concentration of 1 ng/mL for IL-1β and 10 ng/mL for TNF-α. From FIG. 27, it is understood that MCP-1 is secreted upon stimulation of the vascular endothelial cells by IL-1β (1 ng/mL), and the secretion of MCP-1 is inhibited by added D-psicose depending on the concentration.

Generally, MCP-1 as one of chemokine, i.e., a cytokine having a migratory activity on various hemocyte components, has a migratory activity on monocytes and therefore takes a physically important role in accumulation of monocytes and macrophages within an inflammation focus. From the clinical point of view, in formation of an arterial sclerosis focus, MCP-1 also takes an important role in migration of cell components to form foam cells subsequent to failures of the vascular endothelial cells. Recently, excessive appearance of MCP-1 in change to a morbid state of arterial sclerosis is indicated with immunity dyeing of the arterial sclerosis focus.

From the experiments described above, it was confirmed that the secretion of chemokine MCP-1 from the vascular endothelial cells was inhibited by ketohexose belonging to the rare saccharides. The appearance of MCP-1 in the arterial sclerosis focus is stimulated by various cytokines, and particularly IL-1β and TNF-α are regarded as important factors. In this connection, the results of the above-described experiments suggest that ketohexose belonging to the rare saccharides inhibits the secretion and stimulation of MCP-1 by at least IL-1β.

Because MCP-1 is indicated as taking an important role in change to a morbid state of arterial sclerosis, the MCP-1 secretion inhibitory effect of ketohexose belonging to the rare saccharides is also important from the viewpoint of preventing arterial sclerosis. Thus, ketohexose is expected to be used as a useful substance for remedy of arterial sclerosis (e.g., a remedy and preventive against arterial sclerosis).

As seen from the foregoing results, ketohexose belonging to the rare saccharides can be solely used as a substance for inhibiting the secretion of MCP-1. Also, there is a possibility that other substances capable of inhibiting the secretion of MCP-1 can be found out from studies on derivatives and glycosides of ketohexose. Further, it is indicated that MCP-1 is related to not only arterial sclerosis, but also to generation of other diseases. For example, MCP-1 is indicated as taking part in the process of causing inflammation at a joint in chronic articular pheumatism. In lung diseases such as asthma, MCP-1 is also related to generation of the diseases through migration of monocytes and activation of monocytes and macrophages. Consequently, ketohexose belonging to the rare saccharides has a potential capability to adjust the disease activity in local inflammation and the diseases attributable to monocytes and macrophages, and hence it is expected as being applied as remedies for a wide range of diseases.

EXAMPLE 11

(Effect of Inhibiting Microglia Migration by Ketohexose)

This Example 11 is concerned with a microglia migration inhibitory substance containing, as an active ingredient, ketohexose belonging to the rare saccharides. Internal organs in a living body are brought to necrosis if blood circulation is stopped for a long time and an ischemia state continues. The ischemia state is necessarily caused when blood circulation is temporarily shut off during a surgery of an internal organ and is resumed after the surgery. Also, the ischemia state is likewise caused when an internal organ is picked out, preserved and then implanted in organ transplantation, etc. The Organ Transplantation Law stipulates the simple cooling method, the sustained perfusion method, the freezing method, etc. Currently, the simple cooling method is most widely employed in clinical fields. In the simple cooling method, a preservative liquid is perfused when an internal organ is picked out, and the picked-out organ is immersed in the cooled preservative liquid. At present, the preservation time is drastically prolonged with a University-of-Wisconsin (UW) liquid, which has been developed by the surgery group of Belzer et al in Wisconsin University, and the UW liquid is primarily used. However, when blood circulation is resumed after the end of preservation, a lesion is developed due to extracellular protease, cytokines, etc. To suppress the lesion, a method of adding various drugs (such as pyrazolotriazin derivative drugs and nitric oxide (NO) secretion inducers) to the perfusion liquid, but it is not yet satisfactory from the clinical point of view (Koji Matsumoto, J Nippon Med Sch Vol. 68, No. 3, 2001).

In view of the above, this Example 11 is intended to confirm a microglia migration inhibitory effect of ketohexose belonging to the rare saccharides, and to study usefulness of ketohexose belonging to the rare saccharides in preservation of internal organs and a possibility of applications of the ketohexose to clinical fields.

In this Example 11 described below, an influence of ketohexose belonging to the rare saccharides upon the number of microglias appearing with ischemia is examined. The results of the examination suggest that ketohexose belonging to the rare saccharides reduces the number of appearing microglias, and hence it is expected to satisfy the usefulness in preservation of brains and internal organs and to realize clinical applications in brain treatment. D-psicose was used as the ketohexose belonging to the rare saccharides. As a brain ischemia model, the bilateral common carotid artery of a male gerbil with weight of about 70 g was shut off for 5 minutes. In this model, neurons in the hippocampus CA1 area of a brain are peculiarly brought to ischemic cell necrosis.

Comparative studies were made on three exemplified groups, i.e., one group not subjected to ischemia (control: Sham), another group subject to ischemia+treatment with physiological saline, and still another group subject to ischemia+treatment with D-psicose.

The D-psicose treatment was performed through the steps of dissolving D-psicose in physiological saline to prepare a D-psicose solution with concentration of 200 mg/mL, and administrating the D-psicose solution to the ischemia model through the femoral vein in units of 200 mg/kg at 5 minuets before ischemia and immediately after the ischemia. The physiological saline treatment was performed by administering only physiological saline instead of the D-psicose solution. After 1 week from the ischemia, perfusion fixation was made and a frozen brain sample of 20 μm was prepared, followed by hematoxyline eosin dyeing.

Figure 28:
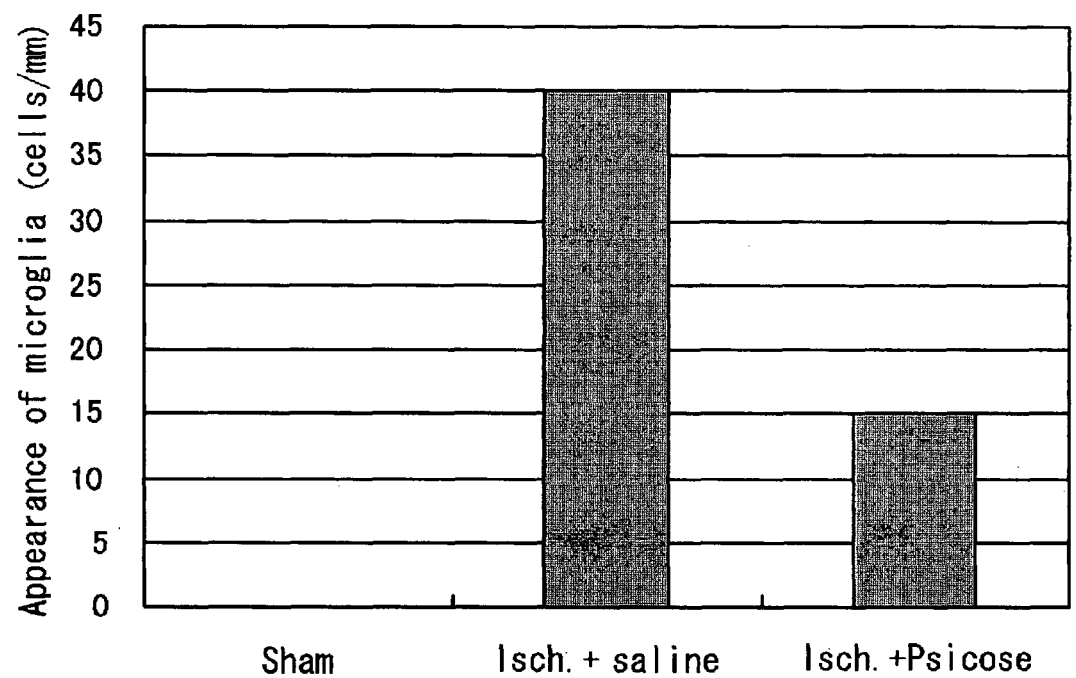
FIG. 28 is a graph, measured in Example 11, showing an influence of D-psicose upon appearance of microglia.

FIG. 28 shows the obtained results. It is understood that the number of appearing microglias, i.e., inflammatory cells, is reduced with the addition of D-psicose, and microglia migration is positively inhibited with the administration of D-psicose. Thus, in this ischemia model, migration of microglias, i.e., inflammatory cells, was inhibited with the administration of D-psicose. It is known that, in temporary brain ischemia, necrosis of hippocampus neurons occurs and a memory failure accompanies as a symptom. Regarding necrosis of neurons with brain ischemia, it is indicated that, even after the ischemic neuron necrosis has been temporarily suppressed by using drugs or the low body-temperature remedy, microglia as one kind of brain glia cells excretes glutamates and active oxygen, thereby taking part in chronic cell necrosis after the treatment. Thus, it can be said that suppressing migration of microglias is also useful for protection against the brain ischemia and preservation intended for transplantation. Accordingly, D-psicose is expected to increase a treatment effect when used in combination with other treatments such as drugs and the low body-temperature remedy.

EXAMPLE 12

(Effect of Ketohexose Regarding Hypoglycemic)

This Example 12 is concerned with a hypoglycemic substance containing, as an active ingredient, ketohexose belonging to the rare saccharides. Diabetes is a national disease which ten millions or more people suffer, including patients with abnormalities in sugar tolerance capability. Diabetes is basically regarded as a peculiar insulin secretion failure attributable to glucose, and hence regarded as a metabolic disease caused from the state where the insulin secretion from the pancreas is weakened, or from insufficiency of the action of secreted insulin. As drugs for promoting the insulin secretion, there are generally known diabetes medicines, such as a sulfonyl urine drug or phenyl alanine derivatives. However, those medicines have various problems in points of side effects, etc. In view of the above, this Example 12 is intended to study usefulness of ketohexose belonging to the rare saccharides in treatment of diabetes and a possibility of applications of the ketohexose to clinical fields. First, a capability of stimulating insulin secretion from pancreas β-cells with ketohexose belonging to the rare saccharides is studied in comparison with glucose. Dynamic behaviors of insulin secretion from the pancreas β-cells under coexistence of glucose and ketohexose belonging to the rare saccharides are then studied. Further, because glucose is supplied through the process of foods being digested, decomposed and absorbed from the intestines, an influence of ketohexose belonging to the rare saccharides upon the absorption of glucose is studied using an intestinal tract. The results of those studies suggest that ketohexose belonging to the rare saccharides is effective in promoting secretion of insulin and it accelerates the secretion of insulin additively (or additionally) particularly when used in combination with glucose, and that because ketohexose belonging to the rare saccharides, which does not affect the sugar metabolism, inhibits the absorption of glucose, usefulness of the ketohexose belonging to the rare saccharides is expected in prevention and treatment of diabetes.

Pancreas β-cell strains INS-1 derived from insulinoma were cultured under the culture medium condition of (DMEM+10% FBS) in accordance with the ordinary method. The INS-1 cells at density of about 70% were pipitted into a 96-well culture dish, and the following experiments were performed. D-psicose was used as the ketohexose belonging to the rare saccharides.

(Experiment 1)

After cultivation for 24 hours with the glucose concentration in the culture medium set to 2.8 mM, 5.6 mM, 11.2 mM and 16.7 mM, the insulin concentration in the culture medium was measured by using an ELISA (insulin kit). As a result, the pancreas β-cell strains INS-1 derived from insulinoma reacted with the glucose concentration in the culture medium, and the insulin secretion from the cells was stimulated. This secretion stimulus reached a plateau at the glucose concentration of 11.2 mM.

(Experiment 2)

Figure 29:
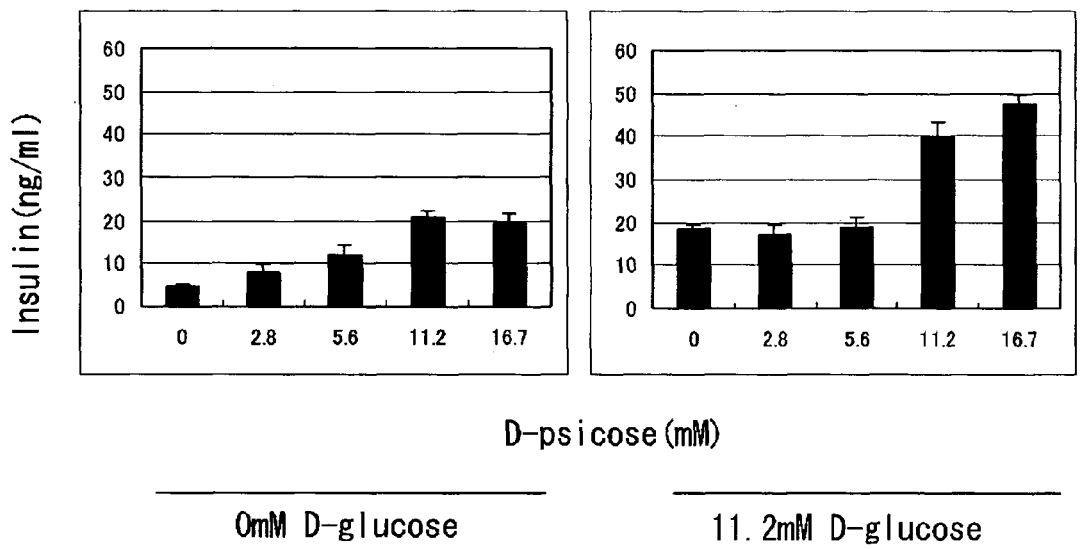
FIG. 29 is a graph, measured in Example 12, showing an influence of D-psicose upon an effect of stimulating secretion of insulin.

By using the ELISA method, the insulin concentration in the culture medium was measured while the D-psicose concentration in the culture medium was changed to 0 mM, 2.8 mM, 5.6 mM, 11.2 mM and 16.7 mM. FIG. 29 shows the measured results. From the results, it was confirmed that, when the pancreas β-cell strains INS-1 were stimulated by D-psicose at various concentrations, insulin was secreted depending on the D-psicose concentration. This secretion stimulus reached a plateau at the D-psicose concentration of 11.2 mM.

(Experiment 3)

While fixing the glucose concentration to 11.2 mM at which the insulin secretion attributable to glucose reached a plateau, D-psicose was further added to change the psicose concentration to 2.8 mM, 5.6 mM, 11.2 mM and 16.7 mM, followed by cultivation for 24 hours. FIG. 29 also shows the results of examining the insulin secretion from the pancreas β-cell strains INS-1 in that state. From those results, it was confirmed that, in spite of holding the insulin secretion attributable to glucose at the maximum stimulus concentration, the insulin secretion into the culture medium was further stimulated in an additive way by additionally increasing the D-psicose concentration.

(Experiment 4)

To clarify an influence of D-psicose upon the absorption of glucose, the influence of D-psicose upon the absorption of glucose was analyzed by using a rat intestinal tract. The absorption of glucose was analyzed by measuring concentrations outside and inside a mucous membrane of an intestinal tract by a quantitative manner based on the glucose oxidase method. How the absorption of glucose changed under coexistence of D-psicose and glucose was measured. Further, how a sugar absorption system changed was analyzed by using an intestinal tract of a rat administrated with D-psicose for a long time.

Figure 30:
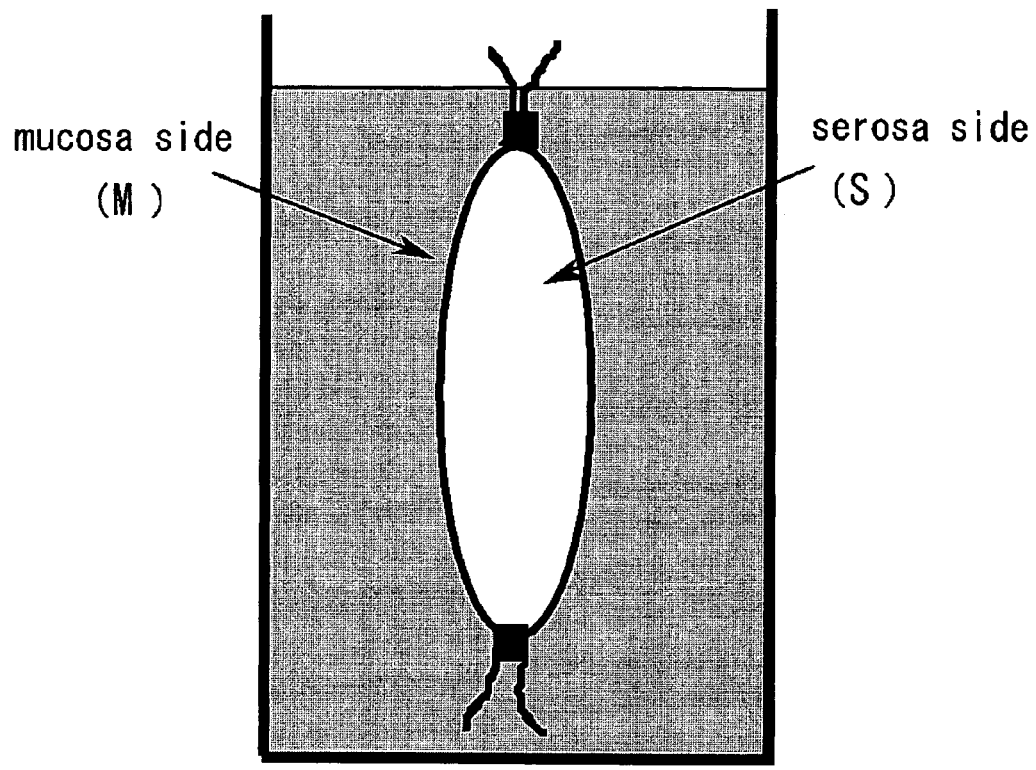
FIG. 30 is an illustration for explaining an experiment example for the reversed intestinal tract used in Example 12.
Figure 31:
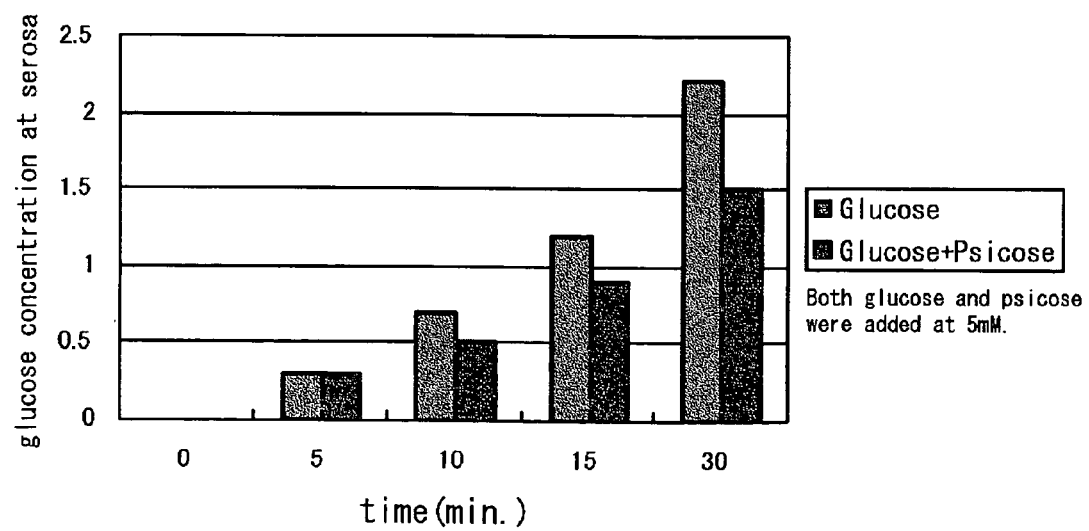
FIG. 31 is a graph, measured in Example 12, showing an influence of D-psicose upon absorption of grape sugar.

As shown in FIG. 30, the reversed intestinal tract of the rat was immersed in a buffer containing glucose. After the lapse of a certain time, the solution on the serous membrane side was sampled and the glucose concentration was measured. By adding D-psicose at various concentrations, an influence of D-psicose upon transport of glucose from the mucous membrane side to the serous membrane side was studied. FIG. 31 shows the obtained results.

As seen from the results, a rise of the glucose concentration on the serous membrane side was significantly inhibited by adding, to the reversed intestinal tract of the rat, D-psicose at concentration comparable to that of glucose. This suggests a possibility that the addition of D-psicose affects the glucose support system in some way. Also, from the above results, it was found that ketohexose belonging to the rare saccharides stimulated the secretion of insulin from the pancreas β-cells. Moreover, by additionally adding ketohexose belonging to the rare saccharides to the cells at the glucose concentration, at which the maximum insulin secretion stimulus was obtained, further insulin secretion was observed. Generally, diabetes is basically regarded as a peculiar insulin secretion failure attributable to glucose. Then, when the insulin secretion based on glucose is insufficient, ketohexose belonging to the rare saccharides is expected to act to effectively promote the insulin secretion. This means confirmation of the findings that ketohexose belonging to the rare saccharides has an effect of stimulating the insulin secretion from the pancreas β-cells, and that ketohexose belonging to the rare saccharides has an effect of enhancing the insulin secretion in the hyperglycemic state. Therefore, ketohexose belonging to the rare saccharides is expected as a substance having a novel action mechanism that is not yet known. It is also expected that, in diabetics who are clinically diagnosed to be hyperglycemic, ketohexose belonging to the rare saccharides promotes the insulin secretion and improves the blood sugar value. The facts that ketohexose belonging to the rare saccharides, which is administrated through the intestine tract, inhibits the absorption of glucose and that ketohexose belonging to the rare saccharides does not affect the sugar metabolism, mean a possibility that the ketohexose inhibits excessive blood sugar in diabetics after meals. Accordingly, the ketohexose is expected as a substance useful for preventing and remedying diabetes. Further, ketohexose belonging to the rare saccharides is confirmed as having an effect of preventing arterial sclerosis which is closely related to diabetes and its complications, and a main death cause of diabetes is arterial sclerosis induced diseases. Hence, ketohexose belonging to the rare saccharides, which has the arterial sclerosis inhibitory effect, is also expected as an epochal diabetes remedy effective in improving the blood sugar value and preventing arterial sclerosis. In addition, ketohexose belonging to the rare saccharides is further expected to be mixed in health aid foods effective in the above-mentioned treatment and in preventing fatness.

EXAMPLE 13

(Influence Upon Rat Blood-Sugar Value with Administration of Rare Saccharide)

(1) Purpose: It is reported that hyperinsulinism caused under a load exerted by administrating D-fructos in large amount for a long period is inhibited with administration of rare saccharides, in particular D-psicose. In this Example 13, the inventors examined how the blood sugar value varied with administration of a rare saccharide.

(2) Method: 1) Administration of rare saccharide: An SD male rat (with weight of about 300 g) was employed in an experiment after fasting for 20 to 24 hours. Nembutal (58 mg/kg BW) was applied to the rat through abdominal administration, and after cutting the neck under anesthesia, a silicon tube was fixedly kept inserted in the jugular vein. A 1-ml syringe was connected to the silicon tube for administration of the rare saccharide.

2) Blood-collecting: Blood was collected by using the 1-ml syringe through the silicon tube inserted in the jugular vein. The blood-collecting was made immediately before the administration of the rare saccharide and then after 5, 10, 15, 20, 25, 30, 60, 120, 180 and 240 minutes from the same.

3) Blood sugar measurement: The blood sugar value in the collected blood was measured by using Antosense II (made by Bayer Medical).

Figure 32:
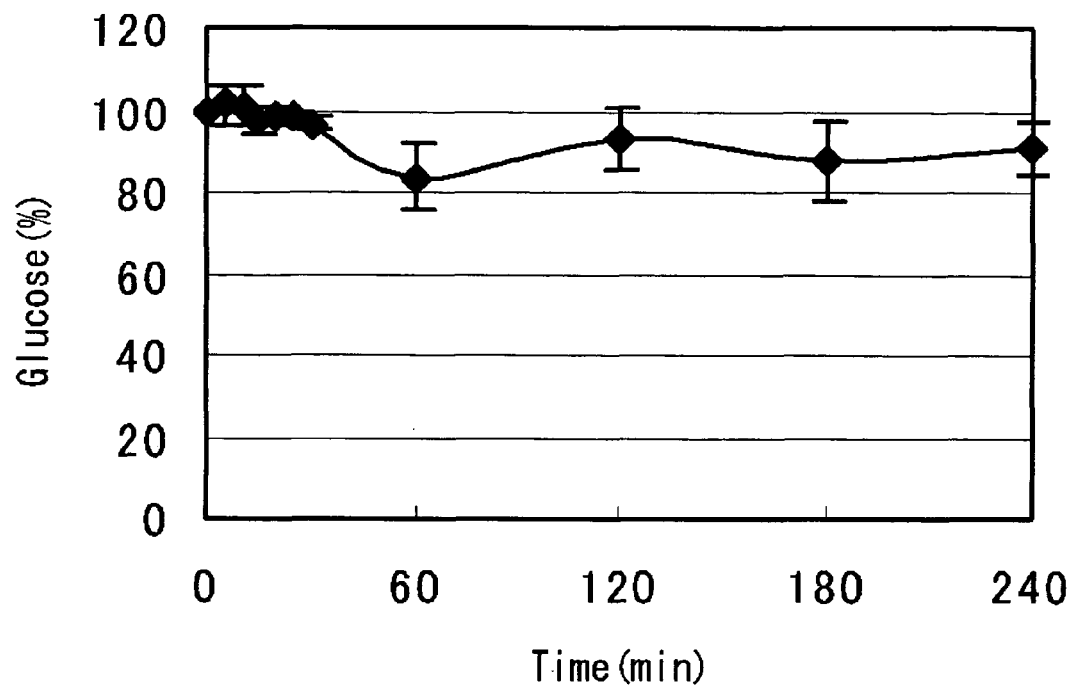
FIG. 32 is a graph, measured in Example 12, showing an influence of application of a rare saccharide upon a rat blood-sugar value, in particular, showing an influence upon blood sugar with application of physiological saline under anesthesia.

(3) Results:

1) Influence upon blood sugar with administration of physiological saline under anesthesia (FIG. 32): First, only physiological saline (0.7 mL) was administrated to three rats through intravenous injection, and influences of anesthesia, etc. upon the blood sugar value were examined. As a result, no remarkable change in the blood sugar value was found with the administration of physiological saline.

Figure 33:
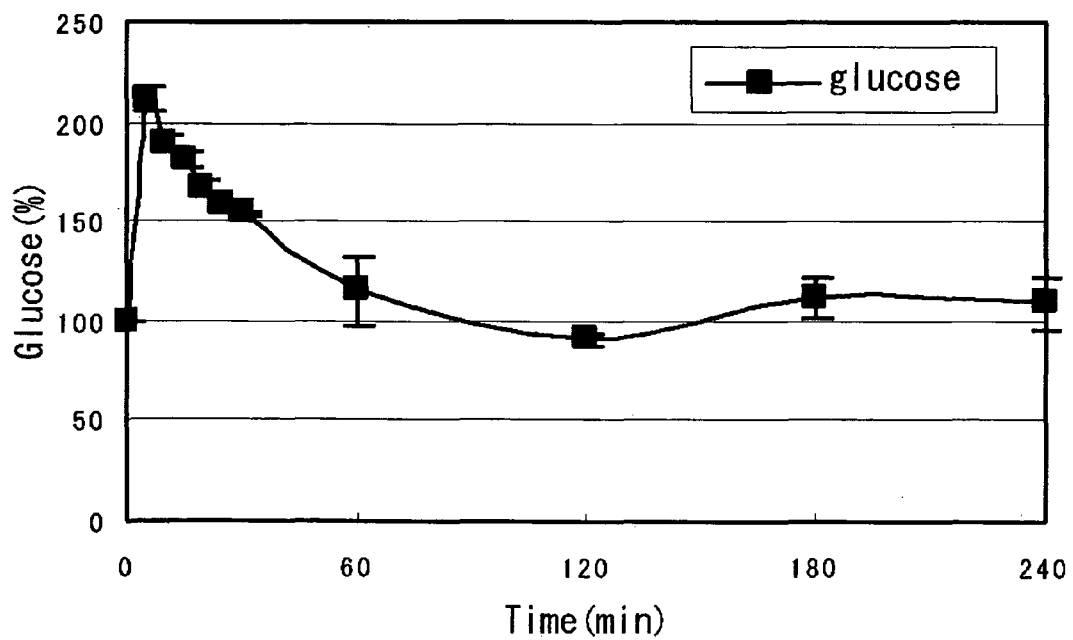
FIG. 33 is a graph, measured in Example 13, showing an influence of application of a rare saccharide upon a rat blood-sugar value, in particular, showing an influence upon blood sugar with application of D-glucose under anesthesia.

2) Influence upon blood sugar value with administration of D-glucose under anesthesia (FIG. 33): D-glucose (200 mg/kg BW) was intravenously injected through the jugular vein, and the blood sugar value was measured before and after the injection (N=2). The blood sugar value was temporarily increased with the administration of D-glucose, and then approached a normal value in about 60 minutes.

Figure 34:
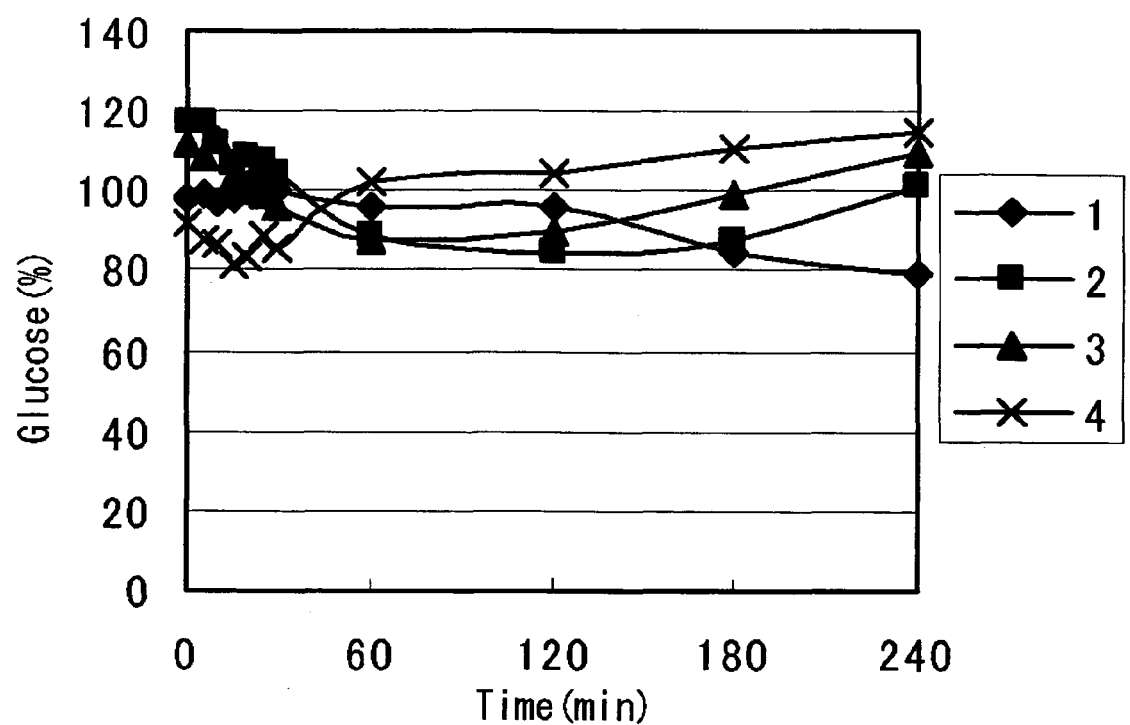
FIG. 34 is a graph, measured in Example 13, showing an influence of application of a rare saccharide upon a rat blood-sugar value, in particular, showing an influence upon blood sugar with application of D-psicose.

3) Influence upon blood sugar value with administration of D-psicose (FIG. 34): Psicose (200 mg/kg BW) was administrated to the rats under anesthesia through intravenous injection, and the blood sugar value was measured (N=4). In two rats, the blood sugar value reduced during a period of 30 to 60 minutes after the administration of the rare saccharide, and then gradually restored to an initial value. In the other two rats, the blood sugar value first reduced and then increased beyond an initial value, or it hardly changed.

(4) Reviews: As a result of the experiments of this Example 13 using the normal rats under anesthesia, it was confirmed that anesthesia with Nembutal and the intravenous administration of physiological saline did not affect the blood sugar value and the D-glucose load. In the experiments of this Example 13, the administration of D-psicose reduced the blood sugar value in a half of the rats during a period of 30 to 60 minutes after the administration, and thereafter the blood sugar value gradually restored to the initial value. In the other two rats, the blood sugar value reduced in an early stage and then increased, or it gradually reduced. From those results, it was found that, though there were individual differences, normal rats caused light hypoglycemic with the administration of the rare saccharide (D-psicose). Studies in future are required to increase the number of animals subjected to experiments for more detailed data analysis. It is also required to study an effect in hyperglycemic rats. In other experiments conducted at the same time using D-allose, no hypoglycemic was found.

EXAMPLE 14

(Hyperglycemic State Relieving Effect of Ketose)

(1) Purpose: Diabetes is a national disease which ten millions or more people suffer, including patients with abnormalities in sugar tolerance capability. Diabetes is basically regarded as a peculiar insulin secretion failure attributable to glucose. In this Example 14, therefore, the inventors study usefulness of, in particular, D-psicose belonging to ketose in treatment of diabetes and a possibility of applications of the ketose to clinical fields. Up to now, the inventors have studied in vitro a capability of stimulating insulin secretion from pancreas β-cells with ketose. The study in this Example 14 is made on influences of D-psicose upon the insulin secretion capability and the sugar metabolism by using rats in neither anesthetic nor restraint state. The study tries to prove in vivo an insulin secretion stimulus effect of ketose from the pancreas β cells and an insulin secretion enhancing effect of ketose in a hyperglycemic state. Thus, this Example 14 is intended to study a possibility of ketose as being a preventive or remedy against diabetes.

(2) Method: 1) Intravenous grape sugar load test (IVGTT) . . . IVGTT was conducted on 8-week old male SD rats by inserting a catheter through the jugular vein. A rare saccharide was administrated to 3 rats, and glucose was administrated to other 3 rats.

Protocol 1

Perform intravenous injection (IV) at 0.5 g/kg (i.e., 0.5 g/1000 g=500 mg/1000 g=0.5 mg/g).

Prepare rare-saccharide and glucose solutions in concentration of 0.5 g/mL (i.e., 0.5 g/1000 ul=500 mg/1000 ul=0.5 mg/ul). Prepare 2 mL of solution for each concentration.

Intravenously inject 200 ul of the solution for a 200 g rat.
Intravenously inject 250 ul of the solution for a 250 g rat.
Inject 300 ul of physiological saline after the intravenous injection.

Collect 150 ul of blood sample.

Abstain each rat from food for 16 hours as pretreatment. Allow to drink water.

Collect blood at 9 points in time, i.e., 0, 5, 10, 15, 20, 25, 30, 45 and 60 minutes.

2) Influence of psicose upon hyperglycemia

IVGTT was conducted on 8-week old male SD rats by inserting a catheter through the jugular vein, injecting 50% glucose at intervals of 20 minutes to make a hyperglycemic state, and then injecting psicose and deoxyglucose. A rare saccharide was administrated to 1 rat, and deoxyglucose was administrated to 1 rat.

Protocol 2

Perform intravenous injection (IV) at 0.5 g/kg (i.e., 0.5 g/1000 g=500 mg/1000 g=0.5 mg/g).

Prepare rare-saccharide and deoxyglucose solutions in concentration of 0.5 g/mL (i.e., 0.5 g/1000 ul=500 mg/1000 ul=0.5 mg/ul). Prepare 2 mL of solution for each concentration.

Intravenously inject 200 ul of the solution for a 200 g rat.
Intravenously inject 250 ul of the solution for a 250 g rat.
Inject 300 ul of physiological saline after the intravenous injection.

Collect 150 ul of blood sample.

Collect blood at 9 points in time, i.e., 0, 5, 10, 15, 20, 25, 30, 45 and 60 minutes.

Figure 35:
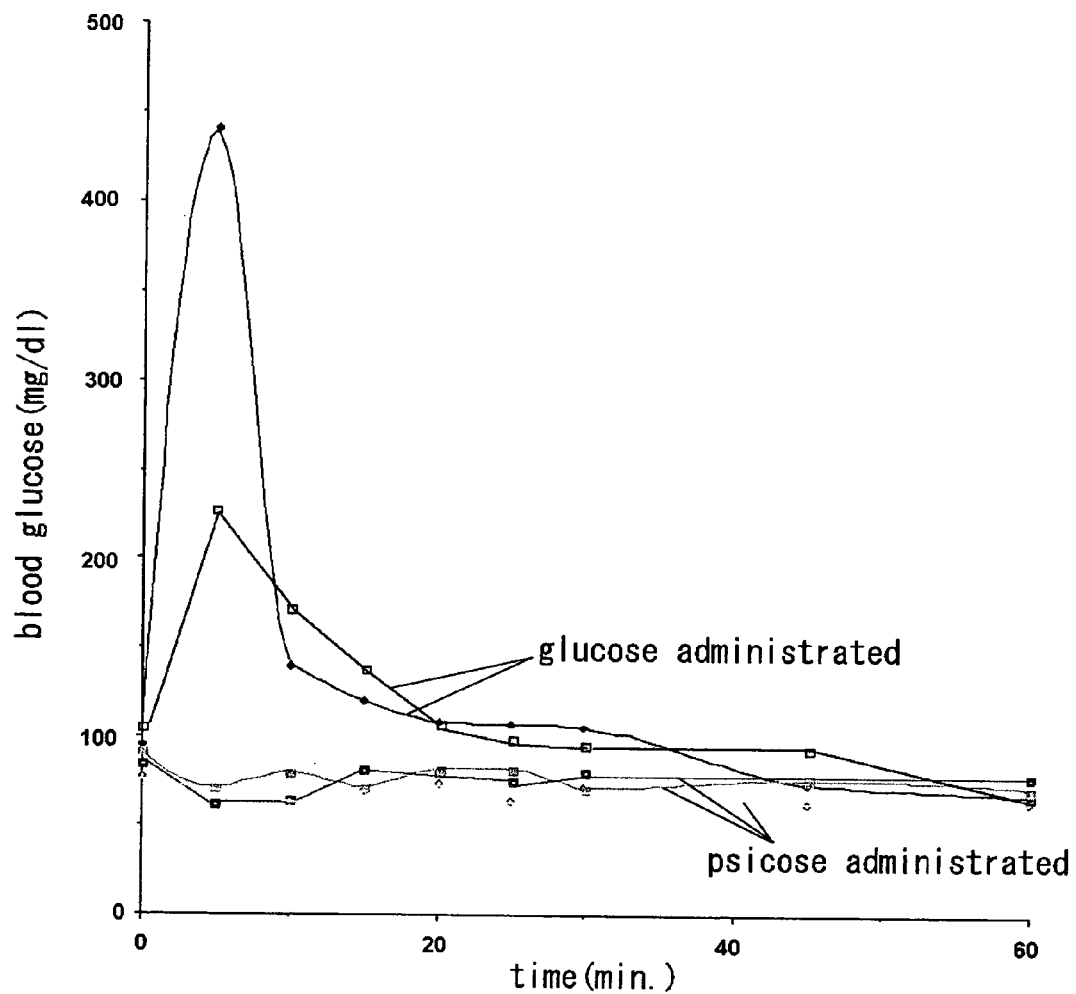
FIG. 35 is a graph, measured in Example 14, showing an influence upon concentration of blood D-glucose in IVGTT in relation to a high blood-sugar condition relieving effect of ketose.
Figure 36:
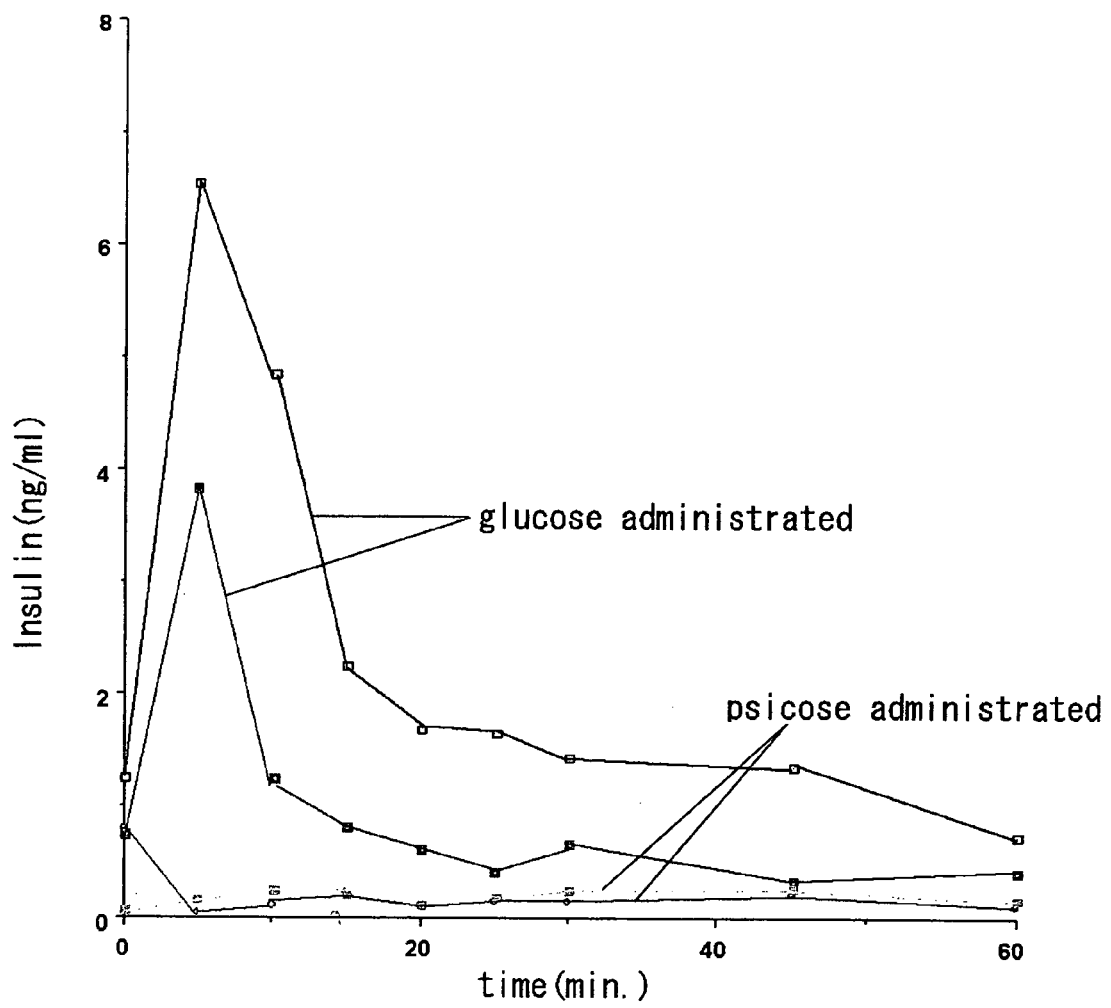
FIG. 36 is a graph, measured in Example 15, showing a dynamic state of insulin in relation to the high blood-sugar condition relieving effect of ketose.

(3) Results: IVGTT . . . Grape sugar (glucose) was used as a control. As shown in FIG. 35, the blood sugar value increased with loading of grape sugar. On the other hand, no rise of the blood sugar value was found with the intravenous injection of psicose. Further, as a result of measuring the insulin concentration in the blood over time during IVGTT, a rise of the insulin concentration was found in match with the rise of the blood sugar value in the grape sugar loaded group. In the psicose administrated group, however, influences upon the insulin secretion were not found because of, presumably, no rise of the blood sugar value (see FIG. 36).

Figure 37:
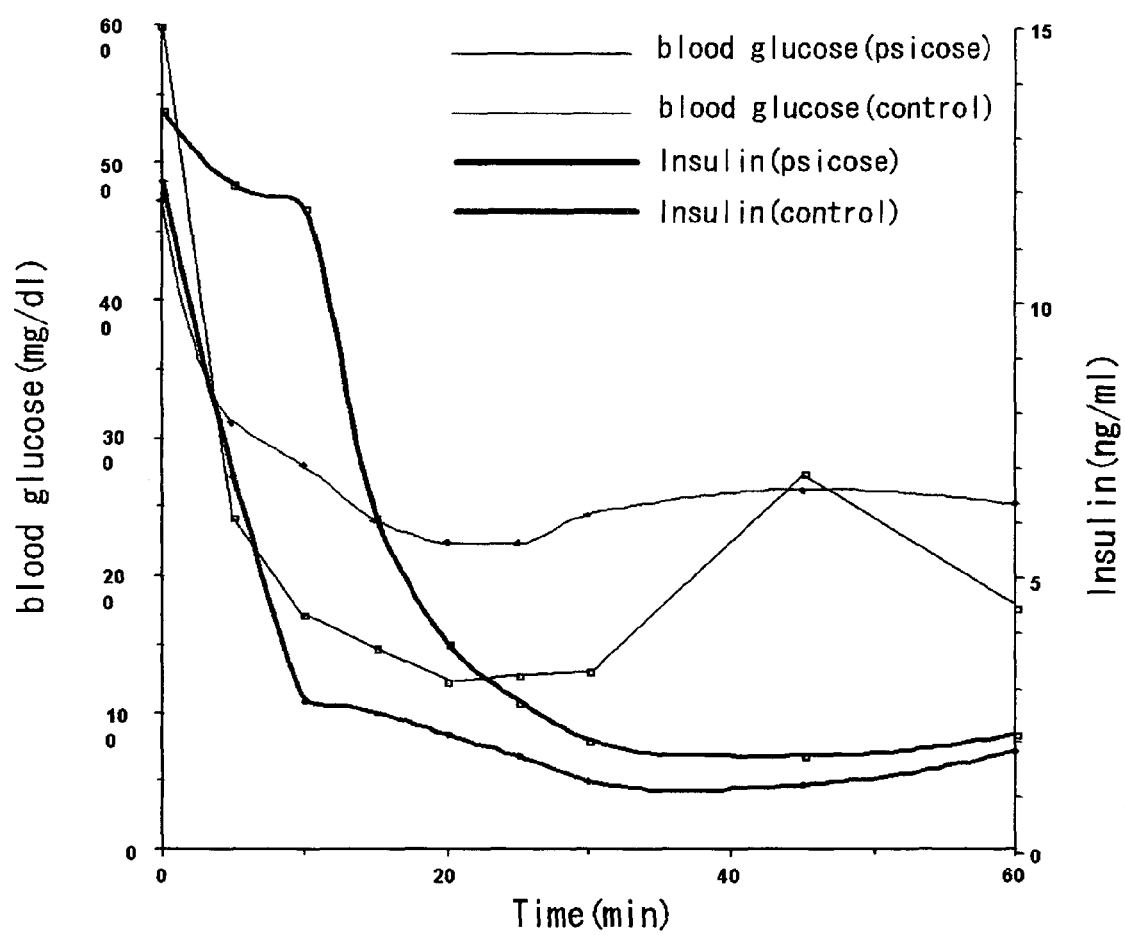
FIG. 37 is a graph, measured in Example 15, showing an effect of D-psicose in a high blood-sugar condition in relation to the high blood-sugar condition relieving effect of ketose.

Since the above results suggest that psicose does not promote the insulin secretion at a normal blood sugar level, the inventors examined an effect of psicose on a rat prepared by continuously administrating grape sugar so as to produce a hyperglycemic state. Deoxyglucose was used as a control. As compared with the control, the blood sugar value reduced more quickly in the psicose administrated group. Also, the measurement of the insulin concentration over time showed an increase in the insulin secretion as compared with the control (see FIG. 37).

(4) Reviews: From the studies made in this Example 14, it was proved in vivo that D-psicose stimulated the insulin secretion from the pancreas β-cells without affecting the sugar metabolism. Also, regarding the insulin secretion effect, it was confirmed that D-psicose acted to promote the insulin secretion in the hyperglycemic state, while the insulin secretion promoting effect was hardly found at a normal blood sugar level and a shift toward a hypoglycemic state was not induced. Although diabetes is basically regarded as a peculiar insulin secretion failure attributable to glucose, the rare saccharide is able to effectively promote the insulin secretion even in such a condition, and therefore it is expected as a substance having a novel action mechanism that is not yet known. Further, there is a possibility that, in diabetics who are clinically diagnosed to be hyperglycemic, D-psicose promotes the insulin secretion and improves the blood sugar value. Accordingly, D-psicose is expected to be used in medicines and/or health aid foods effective in treatment of diabetes.

EXAMPLE 15

(Effect of Rare Saccharide Against Saccharification of Protein)

(1) Purpose: In a persistent hyperglycemic state of diabetics, a non-enzymatic sugar adding reaction (saccharification) of protein is accelerated in a living body. This reaction forms advanced glycation end products (AGE) via Amadori products, etc. (i.e., prophase products), increases oxidation stresses, and eventually developing blood vessel complications, such as retinal diseases and kidney failures attributable to diabetes. In view of the above, this Example 15 is intended to study whether the rare saccharides have an effect of inhibiting saccharification and oxidation stresses in the hyperglycemic state.

Figure 38:
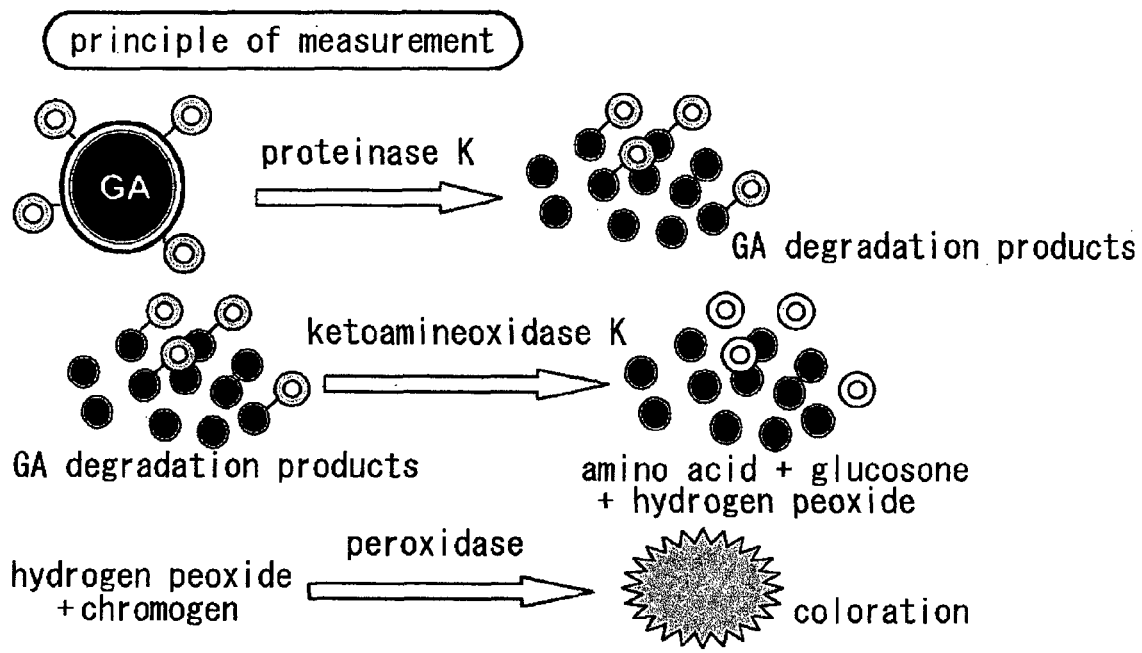
FIG. 38 is an illustration for explaining the GA measurement principle in relation to a study, performed in Example 15, for confirming whether a rare saccharide has a saccharification inhibitory effect in the high blood-sugar condition.

(2) Method: After fragmenting albumin into amino acids by using protease K, i.e., glycoalbumin (GA) measurement reagent (made by Oriental Yeast Co., Ltd.), glycolysine was measured by using ketoamine oxydase (see FIG. 38). Glycation of human albumin with various rare saccharides was examined. A sample was prepared through the steps of dissolving 3 g/dl of pure human albumin in PBS and then dissolving each of the rare saccharides so as to prepare a solution in final concentration of 55.5 mM. The prepared solution was filtrated with a filter of 0.25 μm mesh and sterilized, followed by incubation at 37° C. for 7 days. During the incubation, the GA concentration (glycolysine concentration) was measured at intervals of exactly 24 hours. Further, similar experiments were conducted by adding each of the rare saccharides in an albumin solution (final concentration 3 g/dl) and a glucose solution (final concentration 55.5 mM) so that each of the rare saccharides had final concentration of 55.5 mM.

Figure 39:
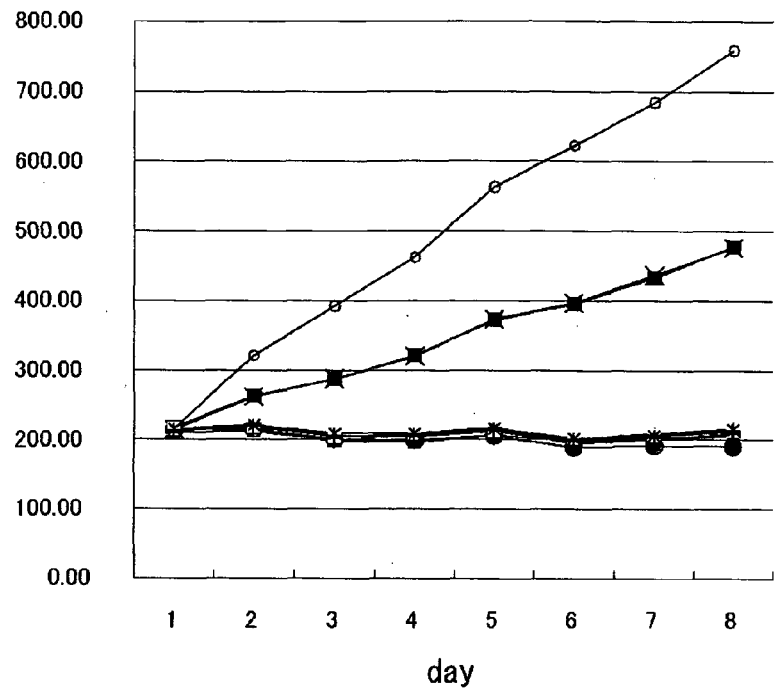
FIG. 39 is a graph showing glycation with a rare saccharide in relation to the study, performed in Example 15, for confirming whether the rare saccharide has a saccharification inhibitory effect in the high blood-sugar condition.

(3) Results: 1) D-allose showed the most significant saccharification reaction and the saccharification rate was about 90 μmol/day. D-glucose and D-mannose showed the next most significant saccharification reaction and the saccharification rate was about 50 μmol/day. For the other rare saccharides (such as D-psicose), glycation of albumin was not found (see FIG. 39).

Figure 40:
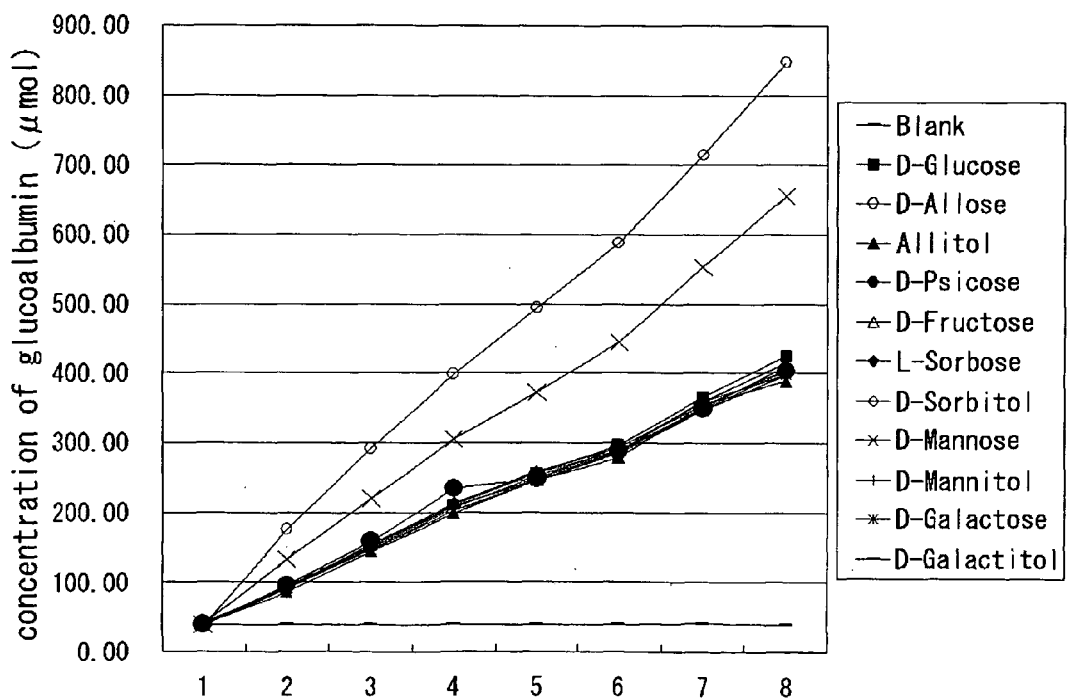
FIG. 40 is a graph showing glycation with a rare saccharide under coexistence of glucose in relation to the study, performed in Example 15, for confirming whether the rare saccharide has a saccharification inhibitory effect in the high blood-sugar condition.

2) Saccharification with rare saccharides under coexistence with glucose . . . Next, the glycoalbumin concentration was measured by adding each of the rare saccharides in an albumin solution (final concentration 3 g/dl) and a D-glucose solution (final concentration 55.5 mM) so that each of the rare saccharides had final concentration of 55.5 mM. As a result, D-allose showed a quick saccharification reaction even under coexistence with glucose. The saccharification rate was about 140 μmol/day (i.e., the sum of the saccharification rates of D-glucose+D-allose) as per the results of the above experiment 1. D-mannose showed the saccharification rate of about 100 μmol/day corresponding to a value obtained by adding the saccharification rate of glucose. For the other rare saccharides (such as D-psicose), an effect of inhibiting glycation was not found (see FIG. 40).

(4) Reviews: In a living body, there occurs non-enzymatic glycation between protein and glucose, for example. A reaction between an amino group and an aldehyde group of protein is important in the initial reaction. The saccharides (D-allose, D-glucose and D-mannose), for which gylcation of albumin was confirmed from the results of studies made here, all belong to alldose. Alidose seems to affect not only the saccharification reaction, but also the polyol metabolism with aldose-reduced enzymes. In clinical inspection, HbAlc, glycoalbumin, etc. are usefully employed as an index for blood sugar control for diabetics. In any case, saccharification reaction products of protein produced with glucose are measured. Saccharification sites are said as being valine in a globin β-chain N-terminus of hemoglobin and 199-, 281-, 439- and 525-th lysines of albumin. Albumin used here for examining the saccharification reaction with the rare saccharides have a larger number of saccharification sites than hemoglobin, and therefore the experimental data was obtained in a relatively short time.

Trying to make similar studies using hemoglobin faces a problem. The saccharification rate is so slow that denaturation of protein overly progresses during incubation and measurement fails. Currently, studies using commercially available hemoglobin powder are in progress.

As seen from the experimental data obtained in this Example 15, D-psicose does not promote saccharification of albumin. Other rare saccharides, such as D-fructose, also do not cause the saccharification, but those saccharides exist abundantly because of having metabolic pathways in the body, and therefore the amount of aldose, etc. in the body increases. Although the metabolism of D-psicose in the human body should be clarified through future experiments, there is a possibility that at least D-psicose does not accelerate the progress of complications attributable to the saccharification reaction, etc. even when administrated in large amount. In addition, because of having the insulin secretion effect as well, D-psicose is expected to be of useful value in treatment of diabetics. On the other hand, a saccharification inhibitory effect of the rare saccharides was not found with the experiments made here using albumin. One of future subjects is to continue similar experiments while changing the concentration of the rare saccharides, and to examine the oxidation inhibitory effect of the rare saccharides.

The present invention has been described above in connection with Examples. Unlike ordinary saccharides, the rare saccharides are not assimilated in the body or, if so, they are assimilated just a little. Also, because of properties affecting the lipid metabolism, the rare saccharides are expected to have an effect of inhibiting accumulation of body fat. Thus, according to the disclosure of the present invention, the rare saccharides are expected to realize applications to various types of medicines, but also to increase an added value of functional foods.

INDUSTRIAL APPLICABILITY

According to the present invention, since the rare saccharides, particularly D-allose and D-psicose, are taken in or act upon cells to modify the function of the cells, it is understood that the rare saccharides can be effectively utilized as a substance having a physiologically active effect.

The invention claimed is:

1. A method of treating diabetes in a patient, comprising:
   administering a composition having D-psicose as an active ingredient to said patient.

2. A method of treating arteriosclerosis in a patient, comprising:
   administering a composition having D-psicose as an active ingredient to said patient.

3. A method of treating necrosis of hippocampus neurons caused by ischemia in a patient, comprising:
   administering a composition having D-allose as an active ingredient to said patient.

* * * * *